United States Patent
Young et al.

(10) Patent No.: US 7,663,021 B2
(45) Date of Patent: Feb. 16, 2010

(54) TRANSGENIC PINEAPPLE PLANTS WITH MODIFIED CAROTENOID LEVELS AND METHODS OF THEIR PRODUCTION

(75) Inventors: Thomas R. Young, Vero Beach, FL (US); Ebrahim Firoozabady, Pleasant Hill, CA (US)

(73) Assignee: Del Monte Fresh Produce Company, Coral Gables, FL (US)

( * ) Notice: Subject to any disclaimer, the term of this patent is extended or adjusted under 35 U.S.C. 154(b) by 263 days.

(21) Appl. No.: 10/536,888

(22) PCT Filed: Dec. 5, 2003

(86) PCT No.: PCT/US03/38664

§ 371 (c)(1),
(2), (4) Date: May 31, 2005

(87) PCT Pub. No.: WO2004/052085

PCT Pub. Date: Jun. 24, 2004

(65) Prior Publication Data

US 2006/0168689 A1 Jul. 27, 2006

Related U.S. Application Data

(60) Provisional application No. 60/431,323, filed on Dec. 6, 2002.

(51) Int. Cl.
C12N 15/52 (2006.01)
C12N 15/55 (2006.01)
C12N 15/82 (2006.01)
A01H 5/00 (2006.01)

(52) U.S. Cl. .............. 800/282; 800/287; 800/298; 435/419; 435/468

(58) Field of Classification Search .................. None
See application file for complete search history.

(56) References Cited

U.S. PATENT DOCUMENTS

| | | |
|---|---|---|
| 5,429,939 A | 7/1995 | Misawa et al. |
| 5,530,188 A | 6/1996 | Ausich et al. |
| 5,530,189 A | 6/1996 | Ausich et al. |
| 5,589,581 A | 12/1996 | Misawa et al. |
| 5,618,988 A | 4/1997 | Hauptmann et al. |
| 5,656,472 A | 8/1997 | Ausich et al. |
| 5,684,238 A | 11/1997 | Ausich et al. |
| 5,744,341 A | 4/1998 | Cunningham, Jr. et al. |
| 5,750,865 A | 5/1998 | Bird et al. |
| 5,792,903 A | 8/1998 | Hirschberg et al. |
| 5,952,543 A | 9/1999 | Firoozabady et al. |
| 5,955,269 A | 9/1999 | Ghai et al. |
| 6,087,563 A | 7/2000 | DellaPenna et al. |
| 6,140,555 A | 10/2000 | Reichert et al. |
| 6,214,575 B1 | 4/2001 | Yano et al. |
| 6,239,331 B1 | 5/2001 | Drake et al. |
| 6,252,141 B1 | 6/2001 | Hirschberg et al. |
| PP12,861 P2 * | 8/2002 | Loison |
| 6,429,356 B1 | 8/2002 | Shewmaker |
| 6,653,530 B1 | 11/2003 | Shewmaker et al. |
| 2002/0092039 A1 | 7/2002 | Shewmaker |
| 2002/0102631 A1 | 8/2002 | Chnningham, Jr. et al. |
| 2002/0142281 A1 | 10/2002 | Broun |
| 2006/0130171 A1 * | 6/2006 | Firoozabady ............... 800/278 |

FOREIGN PATENT DOCUMENTS

| | | |
|---|---|---|
| EP | 0 393 690 A1 | 10/1990 |
| EP | 0 769 551 A1 | 4/1997 |
| WO | WO 91/13078 A1 | 9/1991 |
| WO | WO 95/06741 A1 | 3/1995 |
| WO | WO 95/18220 A1 | 7/1995 |
| WO | WO 96/06172 A1 | 2/1996 |
| WO | WO 96/13149 | 5/1996 |
| WO | WO 98/36637 A1 | 8/1998 |
| WO | WO 99/15003 A1 | 4/1999 |
| WO | WO 99/19499 A1 | 4/1999 |
| WO | WO 99/55889 A2 | 11/1999 |
| WO | WO 99/58644 A1 | 11/1999 |
| WO | WO 00/15813 A1 | 3/2000 |
| WO | WO 00/28005 | 5/2000 |
| WO | WO 00/53768 A1 | 9/2000 |
| WO | WO 01/33943 A1 | 5/2001 |
| WO | WO 01/35727 A1 | 5/2001 |
| WO | WO 01/36597 A1 | 5/2001 |
| WO | WO 01/44276 A2 | 6/2001 |
| WO | WO 01/88169 A2 | 11/2001 |
| WO | WO 02/10398 A2 | 2/2002 |
| WO | WO 02/14523 A2 | 2/2002 |
| WO | WO 02/18617 A2 | 3/2002 |
| WO | WO 02/20815 A2 | 3/2002 |
| WO | WO 2004/052085 A1 | 6/2004 |
| WO | WO 2004/053082 A2 | 6/2004 |
| WO | WO 2004/063359 A2 | 7/2004 |

(Continued)

OTHER PUBLICATIONS

Bird C. et al. Bio/Technology, Jul. 1991 vol. 9, No. 7, pp. 635-639.*
Bramley P. et al. The Plant Journal; 1992, vol. 2 No. 3, pp. 343-349.*
Bartley et al. The Journal of Biological Chemistry; Dec. 5, 1993, vol. 268. No. 34 pp. 25718-25721.*
Ye et al. (2000) Science, 287: pp. 303-305.*
Aitken et al. (1995) "A cDNA Encoding Geranylgeranyl Pyrophosphate Synthase from White Lupin." *Plant Physiol,.* 108: 837-838.

(Continued)

*Primary Examiner*—Russell Kallis
(74) *Attorney, Agent, or Firm*—Quine Intellectual Property Law Group, P.C.

(57) ABSTRACT

The present invention provides methods of transforming pineapple cells and plants with carotenoid biosynthetic polypeptide expression regulators that control the accumulation of carotenoids in the transformed cells, and in certain embodiments, the coloration of those cells. The invention also provides for the regeneration of pineapple plants from the transformed cells. In addition, the invention provides pineapple cells and plants that include introduced carotenoid biosynthetic polypeptide expression regulators.

26 Claims, 3 Drawing Sheets

OTHER PUBLICATIONS

Aracri et al. (1994) "Sequence of the Phytoene Desaturase Locus of Tomato." *Plant Physiol.*, 106: 789.

Armstrong (1994) "Eubacteria show their true colors: genetics of carotenoid pigment biosynthesis from microbes to plants" *Journal of Bacteriology*, 176(16): 4795-4802.

Armstrong et al. (1989) "Nucleotide sequence, organization, and nature of the protein products of the carotenoid biosynthesis gene cluster of Rhodobacter capsulatus," *Mol. Gen. Genet*, 216(2-3):254-268.

Armstrong et al. (1990) "Conserved enzymes mediate the early reactions of carotenoid biosynthesis in nonphotosynthetic and photosynthetic prokaryotes." *Proceeding of the National Academy of Sciences, USA*, 87: 9975-9979.

Badillo et al. (1995) "Structure of a functional geranylgeranyl pyrophosphate synthase gene from *Capsicum annuum*," *Plant Mol. Biol.*,27(2):425-428.

Bartley et al. (1991) "Molecular cloning and expression in photosynthetic bacteria of a soybean cDNA coding for phytoene desaturase, an enzyme of the carotenoid biosynthesis pathway." *Proceeding of the National Academy of Sciences, USA*, 88(15): 6532-6536.

Bartley et al. (1992) "A tomato gene expressed during fruit ripening encodes an enzyme of the carotenoid biosynthesis pathway," *J. Biol. Chem.*, 267(8):5036-5039.

Bartley et al. (1993) "cDNA cloning, expression during development, and genome mapping of PSY2, a second tomato gene encoding phytoene synthase," *J. Biol. Chem.*, 268 (34):25718-25721.

Bird et al. (1991) "Using antisense RNA to study gene function: inhibition of carotenoid biosynthesis in transgenic tomatoes," *Bio/Technology* 9(7):635-639.

Bramley et al. (1992) "Biochemical characterization of transgenic tomato plants in which carotenoid synthesis has been inhibited through the expression of antisense RNA to pTOM5," *Plant Journal*, 2(3):343-349.

Breitenbach et al. (1999) "Catalytic properties of an expressed and purified higher plant type zeta-carotene desaturase from *Capsicum annuum*," *Eur. J. Biochem,*. 265(1):376-383.

Britton. "Biosynthesis of carotenoids," p. 133-182, in T. W. Goodwin (Ed.), *Plant Pigments*, Academic Press, Inc. (1988).

Cunningham et al. (1996) "Functional analysis of the beta and epsilon lycopene cyclase enzymes of Arabidopsis reveals a mechanism for control of cyclic carotenoid formation," *Plant Cell*, 8(9):1613-1626.

Cunningham et al. (2001) "One ring or two? Determination of ring number in carotenoids by lycopene varepsilon-cyclases," *Proc. Natl. Acad. Sci. U.S.A.*, 98(5):2905-2910.

Firoozabady and Moy (2004) "Regeneration of pineapple plants via somatic embryogenesis and organogenesis," *In Vitro Cellular and Developmental Biology—Plant*, 40(1):67-74.

Fraser et al. (2002) "Evaluation of transgenic tomato plants expressing an additional phytoene synthase in a fruit-specific manner." *Proceeding of the National Academy of Sciences*, USA, 99(2): 1092-1097.

Fray and Grierson. (1993) "Identification and genetic analysis of normal and mutant phytoene synthase genes of tomato by sequencing, complementation and co-suppression," *Plant Mol. Biol.*, 22(4):589-602.

Giuliano et al. (1993) "Regulation of carotenoid biosynthesis during tomato development," *Plant Cell*, 5(4):379-387.

Hable et al. (1995) "Maize phytoene desaturase maps near the viviparous5 locus," *Plant Physiol.*, 108(3):1329-1330.

Hahn et al. (1996) "Open reading frame 176 in the photosynthesis gene cluster of *Rhodobacter capsulatus* encodes idi, a gene for isopentenyl diphosphate isomerase," *J. Bacteriol.* 178(3):619-624.

Harker et al. (1997) "Biosynthesis of ketocarotenoids in transgenic cyanobacteria expressing the algal gene for beta-C-4-oxygenase, crtO," *FEBS Lett.*, 404(2-3):129-134.

Hoshino et al. (1993) "Molecular cloning and sequence analysis of the crtB gene of *Thermus thermophilus* HB27, an extreme thermophile producing carotenoid pigments," *Appl. Environ. Microbiol.* 59(9):3150-3153.

Hugueney et al. (1995) "Metabolism of cyclic carotenoids: a model for the alteration of this biosynthetic pathway in *Capsicum annuum* chromoplasts," *The Plant Journal*, 8(3):417-424.

Hundle et al. (1993) "In vitro expression and activity of lycopene cyclase and beta-carotene hydroxylase from *Erwinia herbicola,"FEBS Lett.*, 315(3):329-334.

Karvouni et al. (1995) "Isolation and characterisation of a melon cDNA clone encoding phytoene synthase," *Plant Mol. Bio.,*. 27(6):1153-1162.

Kim et al. (2001) "Isolation and characterization of cDNAs encoding beta-carotene hydroxylase in Citrus," *Plant Sci.*, 161(5):1005-1010.

Li et al. (1996) "Cloning and characterization of a maize cDNA encoding phytoene desaturase, an enzyme of the carotenoid biosynthetic pathway," *Plant Mol. Biol.*, 30(2):269-279.

Mangels et al. (1993) "Carotenoid content of fruits and vegetables: an evaluation of analytic data," *J. Am. Diet. Assoc.*, 93(3):284-296.

Misawa et al. (1990) "Elucidation of the *Erwinia uredovora* Carotenoid Biosynthetic Pathway of Funstional Analysis of Gene Products Expressed in *Escherichia coli*." *Journal of Bacterolog,y* 172(12): 6704-6712.

Misawa et al. (1995) "Structure and Functional Analysis of a Marine Bacterial Cartenoid Biosynthesis Gene Cluster and Astaxanthin Biosynthesic Pathway Proposed at the Gene Level." *Journal of Bacteriology*, 177(22): 6575-6584.

Pecker et al. (1992) A single polypeptide catalyzing the conversion of phytoene to zeta-carotene is transcriptionally regulated during tomato fruit ripening,. *Proceeding of the National Academy of Sciences, USA*, 89(11): 4962-4966.

Pfander (1992) "Carotenoids: an overview," *Meth. Enzymol.*, 213:3-13.

Ray et al. (1987) "Sequence of pTOM5, a ripening related cDNA from tomato," *Nucleic Acids Res.*, 15(24):10587.

Ray et al. (1992) "Cloning and characterization of a gene involved in phytoene synthesis from tomato," *Plant Mol. Biol.*, 19(3):401-404.

Romer et al. (1993) "Expression of the genes encoding the early carotenoid biosynthetic enzymes in *Capsicum annuum*," *Biochem. Biophys. Res. Commun.*, 196 (3):1414-1421.

Ronen et al. (2000) "An alternative pathway to beta-carotene formation in plant chromoplasts discovered by map-based cloning of beta and old-gold color mutations in tomato." *Proceeding of the National Academy of Sciences, USA*, 97(20): 11102-11107.

Scolnik and Bartely (1994) "Nucleotide Sequences of an Arabidopsis cDNA for Geranylgeranyl Pyrophosphate Synthase." *Plant Physiol*, 104:1469-1470.

Theologis et al. (2000) "Sequence and analysis of chromosome 1 of the plant *Arabidopsis thaliana*," *Nature*, 408(6814):816-820.

Zhu et al. (1997) "Cloning and functional expression of a novel geranylgeranyl pyrophosphate synthase gene from *Arabidopsis thaliana* in *Escherichia coli*," *Plant Cell Physiol.*, 38(3):357-361.

Armstrong (1995) "Genetic Analysis and regulation of carotenoid biosynthesis," in Blankenship et al. (Eds.), *Anoxygenic photosynthetic bacteria; advances in photosynthesis*, Kluwer Academic Publishers, vol. 2:1135-1157.

Armstrong et al.. (1993) "Evolutionary conservation and structural similarities of carotenoid biosynthesis gene products from photosynthetic and nonphotosynthetic organisms," *Methods Enzymol.*, 214:297-311.

Bramley and Mackenzie. (1988) "Regulation of carotenoid biosynthesis," *Curr. Top. Cell Regul.,*. 29:291-343.

Hugueney et al. (1992) "Characterization and molecular cloning of a flavoprotein catalyzing the synthesis of phytofluene and zeta-carotene in Capsicum chromoplasts," *Eur. J. Biochem,*. 209(1):399-407.

Ikoma et al. (2001) "Expression of a phytoene synthase gene and characteristic carotenoid accumulation during citrus fruit development," *Physiol. Plantarum.* 111:232-238.

Burkhardt et al. (1997) "Transgenic rice (*Oryza sativa*) endosperm expressing daffodil (*Narcissus pseudonarcissus*) phytoene synthase accumulates phytoene, a key intermediate of provitamin A biosynthesis," *The Plant Journal*, 11(5):1071-1078.

Romer et al. (2000) "Elevation of the provitamin A content of transgenic tomato plants," *Nature Biotechnology*, 18:666-669.

Costa et al. (2002) "An evaluation of factors affecting the efficiency of *agrobacterium*-mediated transformation of *Citurs paradisi*

(macf.) and production of transgenic plants containing carotenoid biosynthetic genes," *Plant Cell Rep.*, 21:365-373.

Rosati et al. (2000) "Metabolic engineering of beta-carotene and lycopene content in tomato fruit," *The Plant Jouranl*, 24(3):413-419.

Rissler & Pogson (2001) Antisense inhibition of the beta-carotene hydroxylase enzyme in *arabidopsis* and the implications for carotenoid accumulation, photoprotection and antenna assembly, *Photosynthesis Research*, 67:127-137.

Sandmann (2001) "Carotenoid biosynthesis and biotechnological application," *Archives of Biochemistry and Biophysics*, 385(1):4-12.

Hirschberg (2001) "Carotenoid biosynthesis in flowering plants," *Current Opinion in Plant Biology*, 4:210-218.

Sripaoraya et al. (2001) "Herbicide-tolerant transgenic pineapple (*Ananas comosus*) produced by microprojectile bombardment," *Annals of Botany*, 88:597-603.

Setiawan et al. (2001) "Carotenoid content of selected Indonesian fruits," *Journal of Food Composition and Analysis*, 14:169-176.

International Search Report for PCT/US03/38664.

Ye et al. (2000) "Engineering the Provitamin A (β-Carotene) Biosynthetic Pathway into (Carotenoid-Free) Rice Endosperm." *Science*, 287: 303-305.

Dewald et al. (1988) "Production of pineapple plants in vitro." *Plant Cell Reports*, 7: 535-537.

Firoozabady et al. (1995) "In vitro plant regeneration and advanced micropropagation methods for pineapple." *In Vitro*, 31: 51 Abstract.

Frulleux et al. (1997) "*Agrobacterium tumefaciens*—mediatated transformation of shoot-buds of chicory." *Plant Cell, Tissue and Organ Culture*, 50: 107-112.

Kiss et al. (1995) "A Novel Method for Rapid Micropropagation of Pineapple." *HortScience*, 30(1): 127-129.

Mezzetti et al. (2002) "Genetic transforamtion of *Vitis vinifera* via organogenesis," *BMC Biotechnology*, 2(18).

Xie and Hong (2002) "*Agrobacterium*-mediated genetic transformation of *Acacia mamgium*." *Plant Cell Reports*, 20: 917-922.

* cited by examiner

US 7,663,021 B2

TRANSGENIC PINEAPPLE PLANTS WITH MODIFIED CAROTENOID LEVELS AND METHODS OF THEIR PRODUCTION

CROSS-REFERENCES TO RELATED APPLICATIONS

This application is the national phase under 35 U.S.C. § 371 of International Application No. PCT/US2003/038664, which has an International filing date of Dec. 5, 2003 and which designated the United States of America, which claims the benefit of U.S. Provisional Application No. 60/431,323, filed Dec. 6, 2002, which are both incorporated by reference in their entirety for all purposes.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Many fruits and vegetables contain an array of phytochemicals that contribute to good health. Epidemiological, clinical, and laboratory studies suggest that various carotenoids reduce the onset of chronic diseases, including coronary heart disease (Barton-Duell (1995) *Endocrinologist* 5:347-356), certain cancers (Giovannucci (1999) *J. Natl. Cancer Inst.*, 91:317-331), and age-related macular degeneration (Seddon et al. (1994) *J. Am. J. Med. Assoc.*, 272:1413-1420). Thus, modulation of carotenoid biosynthesis in plants by genetic manipulation should affect the nutritional quality of the crop.

Pineapple plants (*Ananas comosus* of the Bromeliaceae family) are tropical monocotyledonous plants that have rigid spiny-margined recurved leaves and short stalks with dense oblong heads of small abortive flowers. The fruit of many varieties of pineapple plants is used for human consumption. Some of these varieties include Smooth Cayenne, Red Spanish, Perolera, Pernambuco, and Primavera. The plant is self-incompatible, with long periods between successive fruit generations. As a consequence, conventional breeding to improve fruit quality and other agronomic traits has been difficult.

From the foregoing discussion, it is apparent that transgenic pineapple plants with modified carotenoid levels are desirable. In particular, pineapple plants having elevated carotenoid levels in fruit tissues would enhance the nutritional quality of this important crop. Further, genetically transformed pineapple plants having altered coloration are desirable, inter alia, for product differentiation. These and a variety of other features of the present invention will become evident upon complete review of the following disclosure.

SUMMARY OF THE INVENTION

The present invention relates to carotenogenesis in pineapple plants. More specifically, this invention provides methods of genetically transforming pineapple cells or plants with expression regulators that modulate carotenoid biosynthesis in those cells or plants. In particular, the invention provides methods of controlling carotenoid accumulation in pineapple cells in addition to methods of altering pineapple plant coloration, especially fruit tissue coloration. Moreover, the invention provides pineapple cells that include introduced carotenoid biosynthetic polypeptide expression regulators that control accumulation of carotenoid in those cells. Pineapple plants that are regenerated from those pineapple cells are also provided.

In one aspect, the invention relates to methods of controlling carotenoid accumulation in at least one pineapple cell (e.g., an embryogenic cell, an organogenic cell, an embryogenic callus cell, an organogenic callus cell, or the like). The methods include introducing at least one carotenoid biosynthetic polypeptide expression regulator into the pineapple cell. The carotenoid biosynthetic polypeptide expression regulator controls accumulation of carotenoid in the pineapple cell by increasing or decreasing accumulation of carotenoid in the pineapple cell relative to an accumulation of carotenoid in a pineapple cell that lacks the carotenoid biosynthetic polypeptide expression regulator. In certain embodiments, the pineapple cell is an organogenic cell produced by culturing at least one meristemic cell (e.g., a non-apical meristemic cell, etc.). In some of these embodiments, culturing comprises culturing the meristemic cell to produce at least one shoot, and culturing at least one explant from the shoot to produce the organogenic cell.

The methods of controlling carotenoid accumulation in at least one pineapple cell optionally further include regenerating at least one pineapple plant from the pineapple cell (e.g., an embryogenic cell, an organogenic cell, etc.). In certain embodiments, for example, the pineapple cell includes a population of pineapple cells and the methods further include: (i) selecting one or more members of the population of pineapple cells that include the carotenoid biosynthetic polypeptide expression regulator; (ii) regenerating one or more pineapple plants from the members; and, (iii) screening the pineapple plants for an accumulation of carotenoid that is altered relative to an accumulation of carotenoid in a pineapple plant that lacks the carotenoid biosynthetic polypeptide expression regulator. In some embodiments, the altered accumulation of carotenoid is substantially specific to fruit tissues of the pineapple plants. The methods also optionally further include micropropagating pineapple plants.

In another aspect, the present invention relates to methods of altering pineapple plant coloration. The methods include introducing at least one carotenoid biosynthetic polypeptide expression regulator into at least one pineapple plant in which the carotenoid biosynthetic polypeptide expression regulator controls accumulation of at least one colored carotenoid (e.g., lycopene, β-carotene, etc.) in the pineapple plant to alter the coloration of the pineapple plant. That is, the carotenoid biosynthetic polypeptide expression regulator increases or decreases accumulation of colored carotenoid in the pineapple plant relative to an accumulation of colored carotenoid in a pineapple plant that lacks the carotenoid biosynthetic polypeptide expression regulator. Typically, carotenoid biosynthetic polypeptide expression regulators are introduced into at least one pineapple cell from which the pineapple plant is regenerated. In some embodiments, the altered coloration is substantially specific to fruit tissues of the pineapple plant. Optionally, these methods further include micropropagating the pineapple plant.

In still another aspect, the present invention provides a pineapple cell (e.g., an embryogenic cell, an organogenic cell, an embryogenic callus cell, an organogenic callus cell, or the like) that includes at least one introduced carotenoid biosynthetic polypeptide expression regulator. The carotenoid biosynthetic polypeptide expression regulator increases or decreases accumulation of carotenoid in the pineapple cell relative to an accumulation of carotenoid in a pineapple cell that lacks the carotenoid biosynthetic polypeptide expression regulator. The invention further provides a pineapple plant that is regenerated from the pineapple cell.

The carotenoid biosynthetic polypeptide expression regulators of the invention optionally include organic (e.g., DNA, RNA, etc.) or inorganic molecules. In some embodiments, for example, carotenoid biosynthetic polypeptide expression regulators include at least one nucleic acid segment that encodes at least one carotenoid biosynthetic polypeptide, which nucleic acid segment stably integrates into the genome of the pineapple cell or plant. Typically, carotenoid biosynthetic polypeptide expression regulators include at least one nucleic acid segment that encodes at least one carotenoid biosynthetic polypeptide, which nucleic acid segment is operably linked to a constitutive or an inducible promoter. In some embodiments, carotenoid biosynthetic polypeptide expression regulators include at least one nucleic acid segment that encodes at least one carotenoid biosynthetic polypeptide, which nucleic acid segment is operably linked to a promoter that promotes fruit-specific expression of the carotenoid biosynthetic polypeptide. For example, carotenoid biosynthetic polypeptide expression regulators typically include at least one nucleic acid segment that encodes at least one carotenoid biosynthetic polypeptide (e.g., a plant carotenoid biosynthetic polypeptide, a bacterial carotenoid biosynthetic polypeptide, an artificially evolved carotenoid biosynthetic polypeptide, etc.) that is optionally selected from, e.g., an isopentenyl diphosphate isomerase, a geranylgeranyl pyrophosphate synthase, a phytoene synthase, a phytoene desaturase, a $\zeta$-carotene desaturase, a lycopene $\beta$-cyclase, a lycopene $\epsilon$-cyclase, a $\beta$-carotene hydroxylase, an $\epsilon$-hydroxylase, or the like. Moreover, carotenoid biosynthetic polypeptide expression regulators optionally include at least one nucleic acid segment that encodes at least one carotenoid biosynthetic polypeptide that is heterologous to the pineapple cell or plant, or is homologous to at least one endogenous carotenoid biosynthetic polypeptide of the pineapple cell or plant.

Carotenoid biosynthetic polypeptide expression regulators include different embodiments that effect carotenoid accumulation in the transgenic pineapple cells and plants of the present invention in various ways. To illustrate, carotenoid biosynthetic polypeptide expression regulators optionally include at least one sense or antisense nucleic acid segment that corresponds to at least a portion of at least one endogenous carotenoid biosynthetic polypeptide gene. Sense and antisense nucleic acid segments can be used, for example, to suppress the expression of a selected carotenoid biosynthetic enzyme from the carotenoid biosynthesis pathway to effect the accumulation of carotenoids that are substrates of the suppressed enzyme. In some embodiments, carotenoid biosynthetic polypeptide expression regulators include at least one nucleic acid segment that encodes at least one carotenoid biosynthetic polypeptide transcription factor, which when expressed in a transformed cell effects elevated expression of a targeted carotenoid biosynthetic gene. In other embodiments, carotenoid biosynthetic polypeptide expression regulators include at least one nucleic acid segment that encodes at least one carotenoid biosynthetic polypeptide promoter and/or at least one carotenoid biosynthetic polypeptide enhancer, which nucleic acid segment homologously recombines with at least one promoter and/or at least one enhancer of at least one endogenous carotenoid biosynthetic polypeptide gene to increase or decrease expression of the gene as desired.

The carotenoid biosynthetic polypeptide expression regulators of the invention are introduced into pineapple cells or plants utilizing essentially any delivery technique. In some embodiments, for example, carotenoid biosynthetic polypeptide expression regulators include at least one nucleic acid segment that is introduced into pineapple cells or tissues using *Agrobacterium*-mediated delivery. In other embodiments, carotenoid biosynthetic polypeptide expression regulators include at least one nucleic acid segment that is introduced into pineapple cells or plants using at least one nucleic acid delivery technique selected from, e.g., pollen-mediated delivery, direct nucleic acid transfer to at least one protoplast of the pineapple cell, microprojectile bombardment, microinjection, macroinjection of inflorescence, whisker-mediated impregnation, laser perforation, ultrasonification, etc. In certain embodiments, carotenoid biosynthetic polypeptide expression regulators are injected into pineapple plants.

DETAILED DISCUSSION OF THE INVENTION

I. Definitions

Figure 1A:
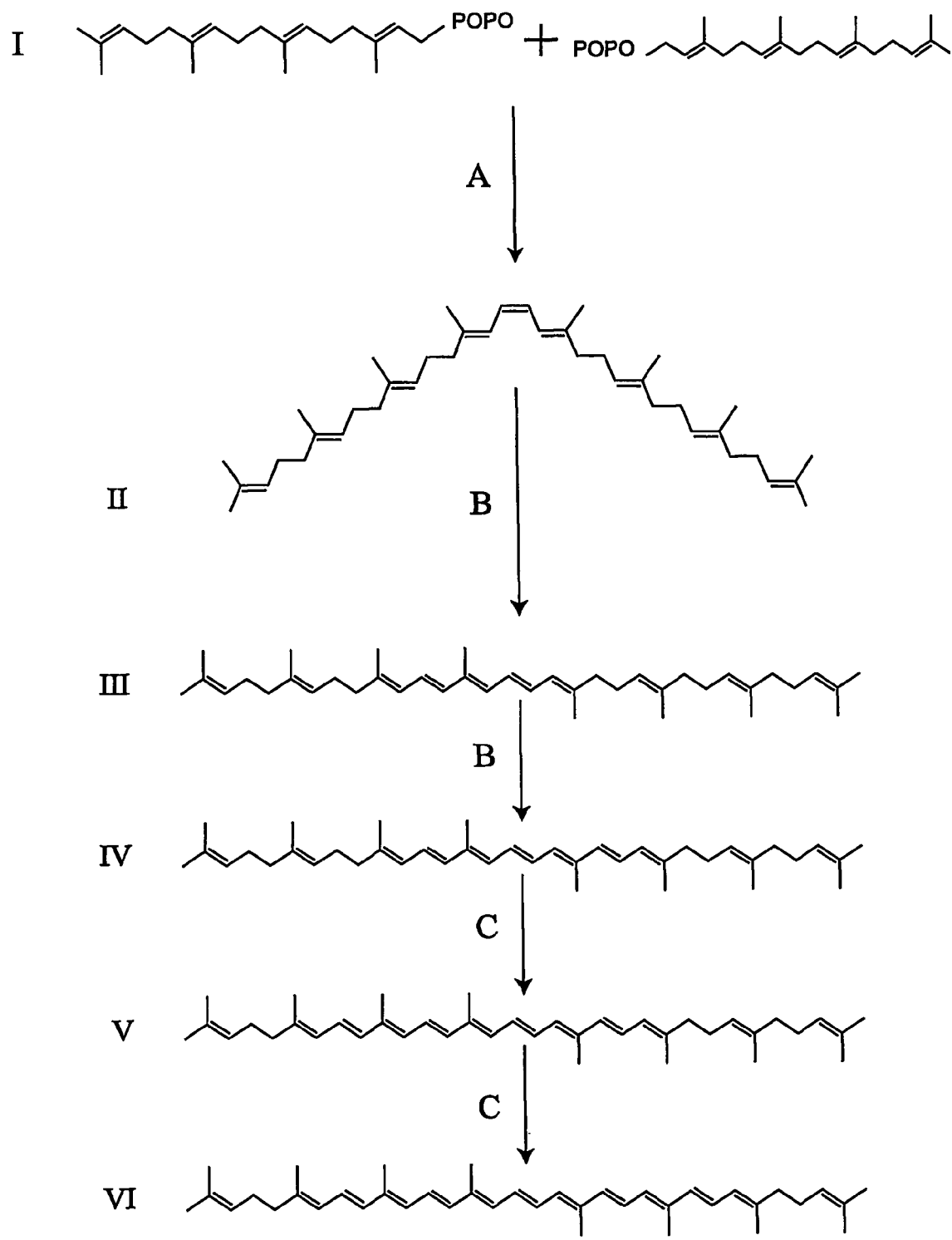
FIGS. 1A-C schematically show aspects of a carotenoid biosynthetic pathway.

Before describing the present invention in detail, it is to be understood that this invention is not limited to particular embodiments. It is also to be understood that the terminology used herein is for the purpose of describing particular embodiments only, and is not intended to be limiting. Units, prefixes, and symbols are denoted in the forms suggested by the International System of Units (SI), unless specified otherwise. Numeric ranges are inclusive of the numbers defining the range. As used in this specification and the appended claims, the singular forms "a", "an" and "the" also include plural referents unless the context clearly dictates otherwise. Thus, for example, reference to "a cell" also includes two or more cells (e.g., in the form of a tissue, etc.), and the like. Further, unless defined otherwise, all technical and scientific terms used herein have the same meaning as commonly understood by one of ordinary skill in the art to which the invention pertains. The terms defined below, and grammatical variants thereof, are more fully defined by reference to the specification in its entirety.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA in solution, such as 2'-O-methylated oligonucleotides), and/or the like. A nucleic acid can be e.g., single-stranded or double-stranded. Unless otherwise indicated, a particular nucleic acid sequence of this invention encompasses complementary sequences, in addition to the sequence explicitly indicated. The term nucleic acid is used interchangeably with, e.g., oligonucleotide, polynucleotide, gene, cDNA, RNAi, and mRNA encoded by a gene.

A "nucleic acid sequence" refers to the order and identity of the nucleotides in a nucleic acid segment.

A "polynucleotide" is a polymer of nucleotides (A, C, T, U, G, etc. or naturally occurring or artificial nucleotide analogues) or a character string representing a polymer of nucleotides, depending on context. Either the given nucleic acid or the complementary nucleic acid can be determined from any specified polynucleotide sequence.

Two nucleic acids "correspond" when they have the same sequence, or when one nucleic acid is complementary to the other, or when one nucleic acid is a subsequence of the other, or when one sequence is derived, by natural or artificial manipulation from the other.

The term "gene" is used broadly to refer to any segment of a nucleic acid associated with a biological function. Thus, genes include coding sequences and optionally, the regulatory sequences required for their expression. Genes also optionally include nonexpressed DNA or RNA segments that, for example, form recognition sequences for other proteins. Genes can be obtained from a variety of sources, including cloning from a source of interest or synthesizing from known or predicted sequence information, and may include sequences designed to have desired parameters.

The term "nucleic acid segment" refers to a polynucleotide or transcribable analog thereof, of at least 25 nucleotides in length, usually at least 100 nucleotides in length, generally at least 200 nucleotides in length, typically at least 300 nucleotides in length, more typically at least 400 nucleotides in length, and most typically at least 500 nucleotides in length. To illustrate, a nucleic acid segment can include a full-length gene (e.g., a gene that encodes a carotenoid biosynthetic polypeptide, such as phytoene synthase or the like), or a subsequence of such a gene.

The term "T-DNA" refers to a nucleic acid segment that can be mobilized and transferred from an *Agrobacterium* into a plant cell to thereby introduce the nucleic acid segment into the plant cell.

The term "linked" generally refers to nucleic acid segments that are contiguous with one another and, where necessary to join two amino acid coding regions, contiguous and in the same reading frame. The term "linked" also encompasses nucleic acids that co-segregate with one another. Further, the term "operably linked" or "operatively linked" refers to a functional linkage between two or more nucleic acid segments. For example, a promoter and a nucleic acid segment that encodes a polypeptide are operably linked when the promoter sequence initiates and mediates transcription of the nucleic acid segment.

The term "carotenoid biosynthetic polypeptide expression regulator" refers to an organic or inorganic molecule that directly or indirectly affects carotenoid biosynthesis in cells into which it is introduced. For example, a carotenoid biosynthetic polypeptide expression regulator can be a nucleic acid segment that encodes a carotenoid biosynthetic polypeptide that increases the accumulation of carotenoids in cells into which it is introduced and expressed.

The term "expression" refers to the transcription and accumulation of sense (mRNA) or antisense RNA derived from the nucleic acid segments of the invention. Expression may also refer to translation of mRNA into a polypeptide, e.g., a carotenoid biosynthetic polypeptide. In some embodiments of the invention, for example, carotenoid biosynthetic polypeptides are expressed in preselected plant storage organs, such as roots, seeds, fruits, etc., leading to enhanced accumulation of one or more carotenoids (e.g., naturally produced carotenoids) in that plant storage organ. Accordingly, the term "fruit-specific expression" refers to the expression of, e.g., introduced carotenoid biosynthetic polypeptides that is substantially limited to fruit tissues of the pineapple plants of the invention, e.g., so as to effect an altered accumulation of carotenoid that is "substantially specific to fruit tissues" of the transformed pineapple plants.

The term "promoter" refers to a recognition site on a DNA sequence or group of DNA sequences that provides an expression control element for a gene and to which RNA polymerase specifically binds and initiates RNA synthesis (transcription) of that gene. The term "constitutive promoter" refers to an unregulated promoter that allows for continual transcription of an associated gene. The term "inducible promoter" refers to a regulated promoter that allows for transcription of an associated gene in the presence of another substance or inducer, such as an extracellular molecule (e.g., a substrate of an enzyme that is encoded by the gene).

The term "selectable marker" includes reference to a gene whose expression allows one to identify cells that comprise the marker gene, such as a nucleic acid segment (e.g., a T-DNA) that includes the marker gene in addition to an encoded polypeptide. To illustrate, a selectable marker gene product may confer herbicide resistance on transformed cells such that upon exposing a population of cells to an effective amount of the herbicide, only those cells that have been transformed remain viable.

The term "sense nucleic acid segment" generally refers to a coding nucleic acid segment. In contrast, the term "antisense nucleic acid segment" typically refers a complement of a sense nucleic acid segment.

The term "transcription factor" refers to any factor that controls the process of transcription (i.e., the making of an RNA copy of a DNA segment). Usually it is an enzyme or other protein, a coenzyme, a vitamin, or another organic molecule.

The term "enhancer" refers to a DNA sequence that positively influences the expression of a gene, even if the enhancer is positioned some distance from that gene.

Two nucleic acids are "recombined" when sequences from each of the two nucleic acids are combined in a progeny nucleic acid.

A nucleic acid segment "stably integrates" into the genome of a pineapple plant or cell when it is non-transiently introduced into that genome. For example, a heterologous nucleic acid segment that is permanently incorporated into a pineapple chromosome is stably integrated into the genome of the corresponding pineapple cell or plant.

The term "transformation" refers to the transfer or introduction of a nucleic acid segment into a plant or plant cell, whether the introduction results in genetically stable inheritance of the nucleic acid segment or only a transient presence of the nucleic acid segment in the genome of the plant or plant cell. Pineapple cells or plants that include the transformed nucleic acid segments are referred to as "transgenic," "recombinant," or "transformed" pineapple cells or plants.

A polynucleotide sequence, such as a nucleic acid segment, is "heterologous" to an organism, or a second polynucleotide sequence, if it originates from another species, or, if from the same species, is modified from its original or native form. For example, a promoter operably linked to a heterologous coding sequence refers to a coding sequence from a species different from that from which the promoter was derived, or, if from the same species, a coding sequence which is different from a naturally occurring allelic variants.

Nucleic acids are "homologous" when they are derived, naturally or artificially, from a common ancestral sequence. Homology is often inferred from sequence similarity between two or more nucleic acids. This occurs naturally as two or more descendent sequences deviate from a common ancestral sequence over time as the result of mutation and natural selection. Artificially homologous sequences may be generated in various ways. For example, a nucleic acid sequence can be synthesized de novo to yield a nucleic acid that differs in sequence from a selected parental nucleic acid sequence. Artificial homology can also be created by artificially recombining one nucleic acid sequence with another, as occurs, e.g., during cloning or chemical mutagenesis, to produce a homologous descendent nucleic acid. Artificial homology may also be created using the redundancy of the genetic code to synthetically adjust some or all of the coding sequences between otherwise dissimilar nucleic acids in such a way as to increase the frequency and length of highly similar stretches of nucleic acids while minimizing resulting changes in amino acid sequences to the encoded gene products. Preferably, such artificial homology is directed to increasing the frequency of identical stretches of sequence of at least three base pairs in length. More preferably, it is directed to increasing the frequency of identical stretches of sequence of at least four base pairs in length. It is generally assumed that two nucleic acids have common ancestry when they demonstrate sequence similarity. However, the exact level of sequence similarity necessary to establish homology varies in the art. In general, for purposes of this disclosure, two nucleic acid sequences are deemed to be homologous when they share enough sequence identity to permit direct recombination to occur between the two sequences, that is, anywhere along the two sequences.

The term "encoding" refers to a polynucleotide sequence encoding one or more amino acids. The term does not require a start or stop codon. An amino acid sequence can be encoded in any reading frame provided by a polynucleotide sequence.

The term "vector" refers to an extra-chromosomal element that is capable of replication in a cell and/or to which other nucleic acid segments can be operatively linked so as to bring about replication of those segments. Such elements may be autonomously replicating sequences, genome integrating sequences, phage or nucleotide sequences, linear or circular, of single- or double-stranded DNA or RNA, derived from any source, in which a number of nucleotide sequences have been joined or recombined into a construct that is capable of introducing nucleic acid segments (e.g., that include one or more promoters and one or more genes that encode carotenoid biosynthetic enzymes) along with appropriate 3' untranslated sequences into a cell. A plasmid is an exemplary vector. Vectors or vector systems (e.g., binary vectors systems, trinary vector systems, or the like) can include elements in addition to, e.g., a gene that encodes a carotenoid biosynthetic enzyme, such as those which facilitate transformation of a pineapple cell or plant, those that allow for enhanced expression of included genes (e.g., promoters) in transformed pineapple cells, those that facilitate selection of transformed pineapple cells (e.g., selectable markers, reporter genes, etc.), or the like. The term "expression vector" refers to an extra-chromosomal element that is capable of regulating the expression of a gene (e.g., a gene encoding a carotenoid biosynthetic polypeptide) when operatively linked to the gene within the vector.

The terms "polypeptide" refers to a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

The term "carotenoid biosynthetic polypeptide" refers to a biocatalyst or enzyme that catalyzes at least one step in the carotenoid biosynthetic pathway. Carotenoid biosynthetic polypeptides include, e.g., geranylgeranyl pyrophosphate synthases, isopentenyl diphosphate isomerases, phytoene synthases, phytoene desaturases, ζ-carotene desaturases, lycopene β-cyclases, lycopene ε-cyclases, β-carotene hydroxylases, ε-hydroxylases, and the like.

A "polypeptide sequence" refers to the order and identity of the amino acids in a polypeptide.

The term "artificially evolved carotenoid biosynthetic polypeptide" refers to a protein-catalyst or enzyme (e.g., a phytoene synthase or the like) created using one or more diversity generating techniques. For example, artificially evolved carotenoid biosynthetic polypeptides employed in the practice of the present invention are optionally produced by recombining (e.g., via recursive recombination or the like) two or more nucleic acids encoding one or more parental carotenoid biosynthetic polypeptides, or by mutating one or more nucleic acids that encode carotenoid biosynthetic polypeptides (e.g., using site directed mutagenesis, cassette mutagenesis, random mutagenesis, recursive ensemble mutagenesis, or the like). A nucleic acid encoding a parental carotenoid biosynthetic polypeptide includes a polynucleotide or gene that, through the mechanisms of transcription and translation, produces an amino acid sequence corresponding to a parental carotenoid biosynthetic polypeptide, e.g., an non-artificially evolved or naturally-occurring phytoene synthase. The term, "artificially evolved carotenoid biosynthetic polypeptide" also embraces chimeric enzymes that include identifiable component sequences (e.g., functional domains, etc.) derived from two or more parents. Artificially evolved carotenoid biosynthetic polypeptides employed in the practice of the present invention are typically evolved, e.g., to yield products with greater efficiency than naturally-occurring carotenoid biosynthetic polypeptides.

The term "endogenous" refers to a substance that is natively produced or synthesized within an organism or system. In a pineapple plant or cell, for example, an endogenous carotenoid biosynthetic polypeptide gene is natively produced (e.g., expressed) within the plant or cell.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using a sequence comparison algorithms or by visual inspection.

A region of "high sequence similarity" refers to a region that is 90% or more identical to a second selected region when aligned for maximal correspondence (e.g., manually or, e.g., using the common program BLAST set to default parameters). A region of "low sequence similarity" is 30% or less identical, more preferably, 40% or less identical to a second selected region, when aligned for maximal correspondence (e.g., manually or using BLAST set with default parameters).

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using, e.g., a sequence comparison algorithm or by visual inspection. Preferably, the substantial identity exists over a region of the sequences that is at least about 50 residues in length, more preferably over a region of at least about 100 residues, and most preferably the sequences are substantially identical over at least about 150 residues. In some embodiments, the sequences are substantially identical over the entire length of the coding regions.

A "subsequence" or "fragment" is any portion of an entire sequence of nucleic acids or amino acids.

The term "genome" refers to the chromosomal nucleic acids of an organism. As used herein, genome also includes the plastid genome (e.g., chloroplast genome, etc.).

The term "*Agrobacterium*" refers to species, subspecies, or strains of the bacterium *Agrobacterium* that are able to mobilize and selectively transfer T-DNA into a plant cell, such as a pineapple cell. For example, the *Agrobacterium* is optionally *Agrobacterium rhizogenes*, but more typically is *Agrobacterium tumefaciens*.

The term "embryogenic cell" refers to a cell from embryogenic tissue or embryogenic callus.

The term "embryogenic callus" refers to tissue or cells that are undifferentiated and without significant structure but with the potential to form a more differentiated tissue (e.g., embryogenic tissue) that can produce embryos and germinate into plants.

The term "embryogenic tissue" refers to tissue having organized structures that include immature somatic embryos. Immature somatic embryos can be matured by culturing them on a maturation medium. Mature somatic embryos can develop into plants upon transfer to a germination medium. A mature somatic embryo is a structure ultimately derived from somatic cells that resembles a zygotic embryo morphologically and developmentally, and that is capable of germinating into a plantlet with both root and shoot poles, when transferred to a suitable growth medium. A "somatic cell" is a cell of a multicellular organism other than gametes.

The term "organogenic cell" refers to a cell from organogenic tissue.

The term "organogenic callus" refers to tissue having an irregular mass of relatively undifferentiated cells, which can arise from, e.g., a single organogenic cell in tissue culture.

The term "organogenic tissue" refers to tissue that is capable of being induced to undergo organogenesis, that is, to form a plant organ such as shoot which can then be induced to develop roots to produce a complete plant.

The term "meristem" refers to a formative plant tissue that comprises cells capable of dividing and giving rise to similar cells or to cells that differentiate to produce tissues and organs.

The term "meristemic cell" refers to a cell from a plant meristem.

The term "non-apical meristemic cell" refers to a meristemic cell that is not from apical meristem, but can be from lateral or axillary merisems and from cells that upon culture of a non-apical meristem explant have become meristematic.

The term "pineapple plant" refers to a plant from the family Bromeliaceae, e.g., *Ananas comosus*. The term "pineapple cell" refers to a cell from a pineapple plant.

The term "regenerating" a pineapple plant refers to the formation of a pineapple plant that includes a rooted shoot.

The term "effective amount" refers to an amount sufficient to achieve a desired result such as the production of a callus or tissue that is embryogenic or organogenic.

The term "carotenoids" refers to the carotene class of hydrocarbons and to their oxygenated derivatives (i.e., xanthophylls).

The term "carotenoid biosynthetic pathway" or "carotenogenesis" refers to the combination of catalytic activities, typically enzyme-mediated, that result in the production of one or more carotenoids.

The term "selecting" refers to a process in which one or more plants or cells are identified as having one or more properties of interest, e.g., a selectable marker, increased or decreased carotenoid levels, altered coloration, etc. For example, a selection process can include placing organisms under conditions where the growth of those with a particular genotype will be favored. To further illustrate, one can screen a population to determine one or more properties of one or more members of the population. If one or more members of the population is/are identified as possessing a property of interest, it is selected. Selection can include the isolation of a member of a population, but this is not necessary. In addition, selection and screening can be, and often are, simultaneous.

The term "screening" refers to a process for separating a population into different groups. Screening processes typically include determining one or more properties of one or more plants or cells. For example, typical screening processes include those in which one or more properties of one or more members of one or more populations is/are determined.

A "population" refers to a collection of at least two different cells or plants.

II. Overview

The present invention relates generally to methods for genetically transforming pineapple cells and plants. The transgenic pineapples of the invention have, inter alia, improved nutritional qualities relative to pre-existing varieties. More specifically, the invention provides genetically transformed pineapple cells and plants obtained by the selective introduction of exogenous carotenoid biosynthetic polypeptide expression regulators into those cells or plants. Carotenoid biosynthetic polypeptide expression regulators control carotenoid accumulation in pineapple cells and in some embodiments, also the coloration of those cells. In addition to modifying carotenoid levels, other traits of interest to consumers, such as fruit sweetness, acidity, texture, and ripening characteristics can also be modified according to the methods described herein. Optionally, other agronomic traits such as improved resistance to bacterial diseases, improved resistance to viral diseases, and/or improved resistance to insects and nematodes are also engineered into the cells and plants of the invention.

In some embodiments, the methods of the invention include the use of suitable pineapple explant material, which is genetically transformed by contacting the explant material with *Agrobacterium* cells. The *Agrobacterium* cells mediate the transfer of nucleic acid segments, e.g., that encode carotenoid biosynthetic polypeptides, into pineapple cells. Other techniques for delivering carotenoid biosynthetic polypeptide expression regulators into cells or plants are also optionally utilized. The present invention further provides culture media suitable for the steps of inducing the formation of embryogenic or organogenic cells for co-cultivation with *Agrobacterium* cells. In certain embodiments, for example, transformed embryogenic cells are selected and embryos are formed therefrom. The embryos can be germinated to form shoots and rooted to produce complete plants.

Various organogenic approaches to transforming and regenerating pineapple plants are also optionally utilized. For example, the invention provides methods of producing transformed pineapple cells that include culturing meristemic pineapple cells (e.g., non-apical meristemic cells, etc.) to produce organogenic pineapple cells. These methods also include introducing carotenoid biosynthetic polypeptide expression regulators into the organogenic pineapple cells to produce transformed organogenic pineapple cells. To further illustrate, the invention also provides methods of producing transformed pineapple cells that include culturing meristemic pineapple cells to produce shoots. These methods also include culturing explants from the shoots to produce organogenic pineapple cells. In certain embodiments, these explants comprise non-apical meristemic pineapple cells. In addition, these methods also include introducing carotenoid biosynthetic polypeptide expression regulators into the organogenic pineapple cells to produce transformed organogenic pineapple cells. These organogenic methods typically further include regenerating pineapple plants from transformed organogenic pineapple cells. All of these and other aspects of the present invention are described below.

III. Carotenoids

In several embodiments herein, coloration of, and/or accumulation of carotenoids in, pineapple cells is controlled by controlling carotenoid expression in those cells. Carotenoids are a class of hydrocarbons (carotenes) and their oxygenated derivatives (xanthophylls). Each of these 40-carbon (C40) terpenoids includes eight joined isoprene (C5) units in which the arrangement of isoprenoid units is reversed at the center of the molecule so that the two central methyl groups are in a 1,6-positional relationship and the remaining non-terminal methyl groups are in a 1,5-positional relationship. Carotenoids, such as α-carotene, β-carotene, apocarotenal (β-apo-8'-carotenal), lycopene (ψ,ψ-carotene), and canthaxanthin (4,4'-diketo-β-carotene) are widely used as food coloring agents, and many carotenoids exhibit pro-vitamin A activity. Trivial names and abbreviations will be used throughout this disclosure, with IUPAC-recommended semisystematic names typically being given in parentheses after first mention of a trivial name.

Figure 1B:
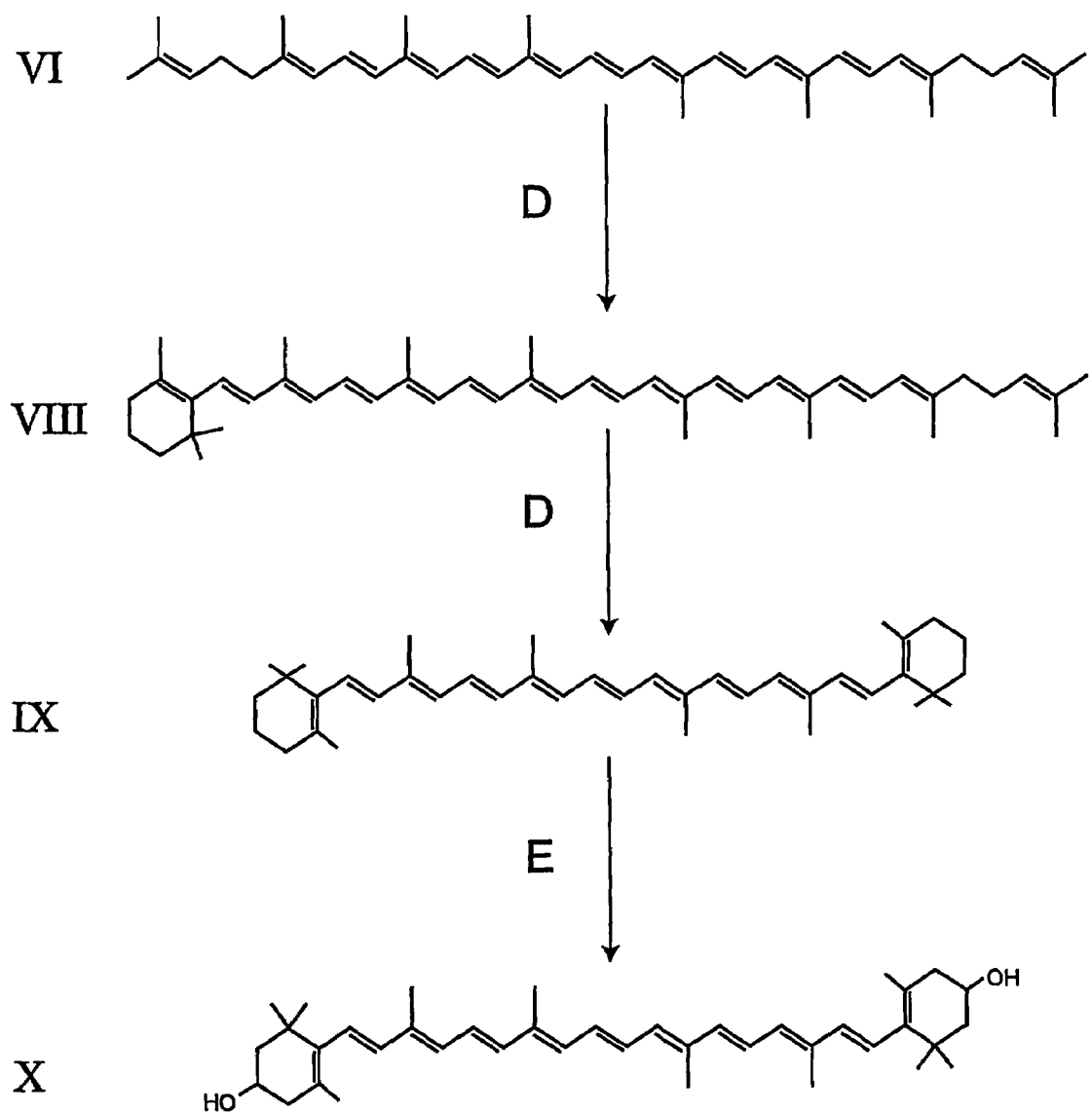
Figure 1C:
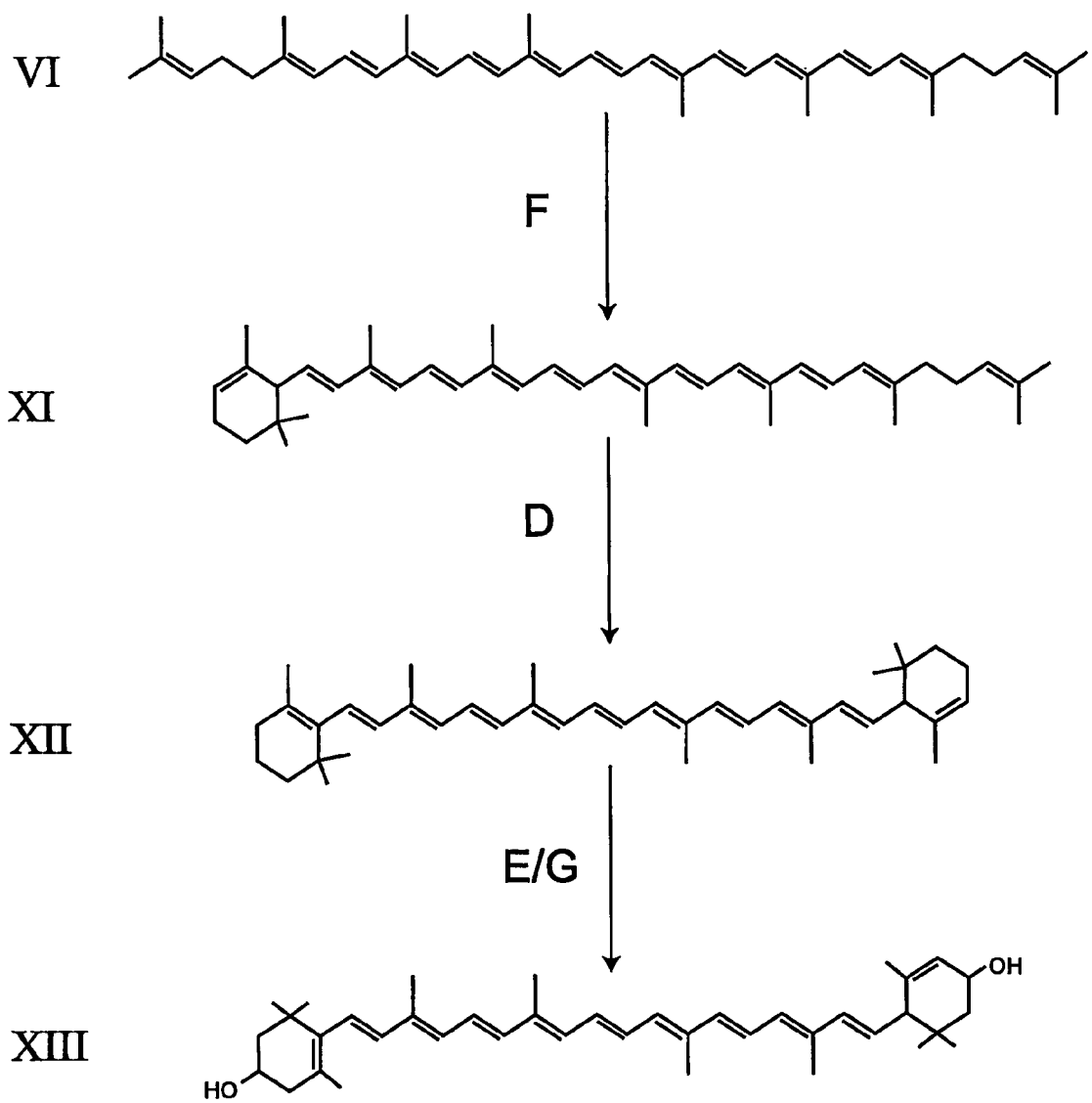

Carotenoids in plants are isoprenoids formed via the mevalonate-independent pathway, which is responsible for isopentenyl diphosphate synthesis in plastids (Fraser et al. (2002) "Evaluation of transgenic tomato plants expressing an additional phytoene synthase in a fruit-specific manner," *Proc. Natl. Acad. Sci. USA*, 99:1092-1097). Geranylgeranyl diphosphate, derived from the ubiquitous isoprenoid pathway, is the precursor of carotenoids in addition to tocopherols and phylloquinone. In particular, geranylgeranyl diphosphate can be produced in various reactions that involve isopentenyl diphosphate and optionally, dimethylallyl diphosphate, geranyl diphosphate, or farnesyl diphosphate. FIGS. 1A-C schematically illustrate aspects of carotenoid biosynthesis. As shown, the dimerization of the 20-carbon atom precursor, geranylgeranyl diphosphate (I) to phytoene (7,8,11,12,7',8',11',12'-octahydro-ψ,ψ-carotene)(II) is the first committed step in carotenoid biosynthesis, catalyzed by the enzyme phytoene synthase (A). Phytoene (II) is itself colorless, but is a precursor for colored carotenoids. The next two enzymes (phytoene desaturase (B) and ζ-carotene desaturase (C)) desaturate phytoene (II) through the intermediate phytofluene (7,7',8,8',11,12-hexahydro-ψ,ψ-carotene)(III), and ζ-carotene (7,8,7',8'-tetrahydro-ζ,ζ-carotene)(IV) through the intermediate neurosporene (7,8-dihydro-ζ,ζ-carotene)(V), respectively.

The product of ζ-carotene desaturase (C) is lycopene (ψ,ψ-carotene)(VI), which can thereafter undergo cyclization to either β-carotene (β,β-carotene)(IX) or α-carotene (XII). Lycopene imparts the characteristic red color to various fruits, such as ripe tomatoes. As shown in FIG. 1B, the cyclization of lycopene (VII) to yield β-carotene (IX) occurs through the intermediate γ-carotene (VIII) in a reaction catalyzed by lycopene β-cyclase (D). Beta-carotene is frequently used as a colorant of products, such as margarine and butter, as a precursor for the production of vitamin A, and has recently been implicated as having preventative effects against certain kinds of cancers. The hydroxylation of β-carotene catalyzed by β-carotene hydroxylase (E) produces zeathanthin (β,β-carotene-3,3'-diol)(X). Zeaxanthin is a yellow pigment that is often used as a colorant in the poultry industry. FIG. 1C schematically illustrates the cyclization of lycopene (VII) to produce α-carotene (XII) through the intermediate δ-carotene (ε,ψ-carotene)(XI), which is catalyzed by lycopene ε-cyclase (F) and lycopene β-cyclase (D). The hydroxylation of α-carotene (XII) to yield lutein (3,3'-dihydroxy-α-carotene)(XIII) is catalyzed by β-carotene hydroxylase (E) and ε-hydroxylase (G). Different cyclases can also be incorporated in the biosynthetic pathway, leading to different cyclization patterns and further derivatizations of the carotenoid structure can be achieved by other down stream modifying enzymes.

In general, the pathway for biosynthesis of the carotenoids has been studied in a variety of organisms and the biosynthetic pathway has been elucidated in organisms ranging from bacteria to higher plants. In leaves, for example, carotenoids are usually present in the grana of chloroplasts where they provide a photoprotective function. Beta-carotene and lutein are the predominant carotenoids, with violaxanthin and neoxanthin being present in smaller amounts. Carotenoids accumulate in developing chromoplasts of flower petals, usually with the disappearance of chlorophylls. As in flower petals, carotenoids appear in fruit chromoplasts as they develop from chloroplasts. Carotenoids are also located in chromoplasts in carrot roots and potato tubers. Beta-carotene is the principal pigment present in both commercial carrots and sweet potatoes, with only small amounts of xanthophylls usually being present. See, e.g., Britton, "Biosynthesis of carotenoids," p. 133-182, in T. W. Goodwin (Ed.), *Plant Pigments*, Academic Press, Inc. (1988).

Investigations have also shown that over expression or inhibition of expression of the plant phytoene synthase (Psy1) gene in transgenic plants can alter carotenoid levels in fruits. See, e.g., Bird et al. (1991) *Biotechnology* 9:635-639; Bramley et al. (1992) *Plant J.* 2:343-349; and Fray et al. (1993) *Plant Mol. Biol.* 22:589-602. Carotenoid biosynthesis genes have also been cloned from a variety of organisms including *Erwinia uredovora* (Misawa et al. (1990) *J. Bacteriol.* 172: 6704-6712; *Erwinia herbicola* (Application WO 91/13078, Armstrong et al. (1990) *Proc. Natl. Acad. Sci., USA* 87:9975-9979); *R. capsulatus* (Armstrong et al. (1989) *Mol. Gen. Genet* 216:254-268, Romer et al. (1993) *Biochem. Biolphys. Res. Commun.* 196:1414-1421); and *Thermus thermophilus* (Hoshino et al. (1993) *Appl. Environ. Microbiol.* 59:3150-3153).

Carotenoids and carotenogenesis are further described in, e.g., Britton et al. (Eds.) *Carotenoids: Spectroscopy, Vol.* 1 Springer-Verlag (1995), Britton et al. (Eds.) *Carotenoids: Synthesis*, Birkhäuser Verlag (1996), Britton et al. (Eds.) *Carotenoids, Vol. 1a: Isolation and Analysis*, Springer-Verlag (1995), Pfander et al. (Eds.) *Key to Carotenoids*, 2nd ed., Springer-Verlag (1987), Passwater et al. (Eds.) *Beta-Carotene and Other Carotenoids: The Antioxidant Family That Protects against Cancer and Heart Disease and Strengthens the Immune System*, Keats Publishing, Inc. (1999), Bauerfeind (Ed.) *Carotenoid as Colorants and Vitamin a Precursors: Technological and Nutritional Applications*, Academic Press, Inc. (1981), Abelson et al. (Eds.) *Carotenoids: Chemistry, Separation, Quantitation, and Antioxidation, Vol.* 213, Academic Press, Inc. (1992), and Abelson et al. (Eds.) *Carotenoids: Metabolism, Genetics, and Biosynthesis, Vol.* 214, Academic Press, Inc. (1993). Additional details relating to carotenoids are provided in, e.g., Bendich (1989) "Carotenoids and the immune response," *J. Nutr.*, 119:112-115, Britton (1995) "Structure and properties of carotenoids in relation to function," *FASEB J.*, 9:1551-1558, Di Mascio et al. (1989) "Lycopene as the most efficient biological carotenoid singlet oxygen quencher," *Arch. Biochem. Biophys.*, 274:532-538, Di Mascio et al. (1991) "Antioxidant defense systems: the role of carotenoids, tocopherols, and thiols," *Am. J. Clin. Nutr.*, 53:194S-200S, Mangels et al. (1993) "Carotenoid content of fruits and vegetables: an evaluation of analytic data," *J.*

*Am. Diet. Assoc.*, 93:284-296, Nishino (1998) "Cancer prevention by carotenoids," *Mutat. Res.*, 402:159-163, Ong et al. (1992) "Natural sources of carotenoids from plants and oils," *Meth. Enzymol.*, 213:142-167, Pfander (1992) "Carotenoids: an overview," *Meth. Enzymol.*, 213:3-13, and Snodderly (1995) "Evidence for protection against age-related macular degeneration by carotenoids and antioxidant vitamins," *Am. J. Clin. Nutr.*, 62(suppl):1448S-1461S.

IV. Target Sequences Encoding Carotenoid Biosynthetic Polypeptides

The carotenoid biosynthetic polypeptide expression regulators of the present invention optionally include a variety of inorganic or organic molecules. In some embodiments, carotenoid biosynthetic polypeptide expression regulators are nucleic acid segments that encode carotenoid biosynthetic polypeptides. Essentially any such nucleic acid segment is optionally utilized to transform the pineapple cells or plants according to the methods described herein. Accordingly, no attempt is made to identify all of the known nucleic acids that can be utilized. Carotenogenesis-related nucleic acid segments that are optionally introduced into pineapple cells or plants typically encode, e.g., isopentenyl diphosphate isomerases, geranylgeranyl pyrophosphate synthases, phytoene synthases, phytoene desaturases, ζ-carotene desaturases, lycopene β-cyclases, lycopene ε-cyclases, β-carotene hydroxylases, ε-hydroxylases, or the like. Reference information pertaining to exemplary carotenoid biosynthesis genes and related sequences that are optionally utilized in performing the methods described herein is provided below.

One organism capable of carotenoid synthesis and a source of genes for such biosynthetic endeavor is *Erwinia herbicola*. *Erwinia herbicola* is a member of a genus of Gram-negative bacteria of the Enterobacteriaceae family that are facultative anaerobes. The genus *Erwinia* is commonly divided into three groups. Of the three, the *herbicola* group includes species (e.g., *Erwinia herbicola*) which typically forms yellow pigments that have been found to be carotenoids. These bacteria exist as saprotrophs on plant surfaces and as secondary organisms in lesions caused by many plant pathogens. They can also be found in soil, water and as opportunistic pathogens in animals, including humans.

Published International Application No. WO 91/13078 (published Sep. 5, 1991) describes the use of genes from *Erwinia herbicola* for the preparation of several carotenoid molecules in several mono- and multicellular organisms. More particularly, Published International Application No. WO 91/13078 describes the enhanced production of phytoene in higher plants using a vector that includes the constitutive cauliflower mosaic virus CaMV 35S promoter and *Agrobacterium tumefaciens*-mediated DNA transfer. Transfer of the gene encoding phytoene synthase linked at its N-terminus to the transit (signal) peptide of tobacco ribulose bisphosphate carboxylase-oxygenase (RUBISCO or RBCS) was also reported as a method of transporting the enzyme into plant chloroplasts where carotenoids are generally synthesized. Published International Application No. WO 91/13078 further describes the use of *Agrobacterium tumefaciens* to transfer a gene that includes the above transit peptide gene and the gene for lycopene cyclase, which converts lycopene into β-carotene in plants to obtain enhanced chloroplast levels of β-carotene. In addition, European Patent Application No. 0 393 690 A1 (published Oct. 24, 1990) reports the use of DNA from another *Erwinia* species, *Erwinia uredovora* 20D3 (ATCC 19321), for preparing carotenoid molecules. To further illustrate, the present invention also optionally utilizes DNA from *Erwinia herbicola* EHO-10 (ATCC 39368 and also referred to as *Escherichia vulneris*), which encodes the enzyme phytoene synthase for the accumulation of carotenoid molecules in higher plant storage organs, such as fruit tissues of pineapple plants.

Additional information regarding carotenoid-related sequences that optionally used in the methods described herein is provide as follows:

Isopentenyl Diphosphate Isomerases

Isopentenyl diphosphate isomerase encoding sequences that are optionally used to transform pineapple cells or plants have been isolated from, e.g., *R. Capsulatus* (Hahn et al. (1996) *J. Bacteriol.* 178:619-624 and the references cited therein), Accession Nos. U48963 and X82627, *Clarkia xantiana* Accession No. U48962, *Arabidopsis thaliana* Accession No. U48961, *Schizosaccharmoyces pombe* Accession No. U21154, *Homo sapiens* Accession No. XI 7025, and *Kluyveromyces lactis* Accession No. X14230.

Geranylgeranyl Pyrophosphate Synthases

Geranylgeranyl pyrophosphate synthase encoding sequences that are optionally used in the transformations described herein include those from, e.g., *E. Uredovora* Misawa et al. (1990) *J. Bacteriol.* 172:6704-6712 and Application WO 91/13078; and from plant sources, including white lupin (Aitken et al. (1995) *Plant Phys.* 108:837-838), bell pepper (Badillo et al. (1995) *Plant Mol. Biol.* 27:425-428) and Arabidopsis (Scolnik and Bartely (1994) *Plant Physiol* 104:1469-1470; Zhu et al. (1997) *Plant Cell Physiol.* 38:357-361).

Phytoene Synthases

Phytoene synthase encoding sequences that are optionally utilized herein include those corresponding to, e.g., Accession number AF220218 corresponding to *Citrus unshiu* phytoene synthase mRNA (Kim et al. "Isolation of a cDNA encoding phytoene synthase from *Citrus*," unpublished), Accession number AB037975 corresponding to *Citrus unshiu* mRNA for phytoene synthase (Ikoma et al. (2001) "Expression of a phytoene synthase gene and characteristic carotenoid accumulation during *citrus* fruit development," *Physiol. Plantarum.* 111:232-238), Accession number AF152892 corresponding to *Citrus x paradisi* phytoene synthase mRNA (Costa et al. "Developmental expression of carotenoid genes in *Citrus*," unpublished), Accession number X68017 corresponding to *C. annuum* psy1 mRNA for phytoene synthase (Romer et al. (1993) "Expression of the genes encoding the early carotenoid biosynthetic enzymes in *Capsicum annuum*," *Biochem. Biophus. Res. Commun.* 196 (3): 1414-1421), Accession number L23424 corresponding to *Lycopersicon esculentum* phytoene synthase (PSY2) mRNA (Bartley et al. (1993) "cDNA cloning, expression during development, and genome mapping of PSY2, a second tomato gene encoding phytoene synthase," *J. Biol. Chem.* 268 (34):25718-25721), Accession number Z37543 corresponding to *C. melo* PSY1 mRNA for phytoene synthase (Karvouni et al. (1995) "Isolation and characterisation of a melon cDNA clone encoding phytoene synthase," *Plant Mol. Biol.* 27(6): 1153-1162), and Accession number M84744 corresponding to tomato phytoene synthetase mRNA (Bartley et al. (1992) "A tomato gene expressed during fruit ripening encodes an enzyme of the carotenoid biosynthesis pathway," *J. Biol. Chem.* 267(8):5036-5039).

Other illustrative sources of phytoene synthase sequences include, e.g., *E. Uredovora, Rhodobacter capsulatus*, and other plants (Misawa et al. (1990) *J. Bacteriol.* 172:6704-6712, Accession No. D90087, Application WO 91/13078, Armstrong et al. (1989) *Mol. Gen. Genet.* 216:254-268, Armstrong "Genetic Analysis and regulation of carotenoid biosynthesis," in Blankenship et al. (Eds.), *Anoxygenic photo-* synthetic bacteria; advances in photosynthesis, Kluwer Academic Publishers, Armstrong et al. (1990) *Proc. Natl. Acad Sci USA* 87:9975-9979, Armstrong et al. (1993) *Methods Enzymol.* 214:297-311, Bartley et al. (1993) *J. Biol. Chem.* 268:27518-27521, Bartley et al. (1992) *J. Biol. Chem.* 267:5036-5039, Bramley et al. (1992) *Plant J.* 2:291-343, Ray et al. (1992) *Plant Mol. Biol.* 19:401-404, Ray et al. (1987) *Nucleic Acids Res.* 15:10587, Romer et al. (1994) *Biochem. Biophys. Res. Commun.* 196:1414-1421, Karvouni et al. (1995) *Plant Molecular Biology* 27:1153-1162, Accession Nos. U32636, Z37543, L37405, X95596, D58420, U32636, Z37543, X78814, X82458, S71770, L27652, L23424, X68017, L25812, M87280, M38424, X69172, X63873, X60441, and Armstrong (1994) *J. Bacteriol.* 1 76:4795-4802 and the references cited therein).

Phytoene Desaturases

Exemplary phytoene desaturase encoding sequences that are optionally utilized to transform pineapple cells or plants according to the methods of the invention include those corresponding to, e.g., Accession number X68058 corresponding to *C. annuum* pds1 mRNA for phytoene desaturase (Hugueney et al. (1992) "Characterization and molecular cloning of a flavoprotein catalyzing the synthesis of phytofluene and zeta-carotene in *Capsicum* chromoplasts," *Eur. J. Biochem.* 209(1):399-407), Accession number X59948 corresponding to *L. esculentum* mRNA for phytoene desaturase (Pecker et al. (1992) "A single polypeptide catalyzing the conversion of phytoene to zeta-carotene is transcriptionally regulated during tomato fruit ripening," *Proc. Natl. Acad. Sci. U.S.A.* 89(11):4962-4966), Accession number L39266 corresponding to *Zea mays* phytoene desaturase mRNA (Hable et al. (1995) "Maize phytoene desaturase maps near the viviparous5 locus," *Plant Physiol.* 108(3):1329-1330), Accession number M88683 corresponding to *Lycopersicon esculentum* phytoene desaturase mRNA (Giuliano et al. (1993) "Regulation of carotenoid biosynthesis during tomato development," *Plant Cell* 5(4):379-387), and Accession number M64704 corresponding to Soybean phytoene desaturase mRNA (Bartley et al. (1991) "Molecular cloning and expression in photosynthetic bacteria of a soybean cDNA coding for phytoene desaturase, an enzyme of the carotenoid biosynthesis pathway," *Proc. Natl. Acad. Sci. U.S.A.* 88(15):6532-6536).

Other illustrative sources of phytoene desaturase sequences include, e.g., those from bacterial sources including *E. uredovora* Misawa et al. (1990) *J. Bacteriol.* 172:6704-6712, and Application WO 91/13078 (Accession Nos. L37405, X95596, D58420, X82458, S71770, and M87280); and from plant sources, including maize (Li et al. (1996) *Plant Mol. Biol.* 30:269-279), tomato (Aracri et al. (1994) *Plant Physiol.* 106:789), and *Capisum annuum* (bell beppers) (Hugueney et al. (1992) *J. Biochem.* 209: 399407), Accession Nos. U37285, X59948, X78271, and X68058).

ζ-Carotene Desaturases

Zeta-carotene desaturase encoding sequences that are optionally utilized herein include those corresponding to, e.g., Accession number AJ319762 corresponding to *Citrus sinensis* mRNA for zeta-carotene desaturase (zds gene) (Marcos et al. "Characterization of Pinalate, a novel *Citrus sinensis* variety with a fruit-specific alteration that results in yellow pigmentation and decreased ABA content," unpublished), Accession number AB072343 corresponding to *Citrus unshiu* Cit-ZCD mRNA for zeta-carotene desaturase (Kasai et al. "*Citrus unshiu* zeta-carotene desaturase," unpublished), Accession number AF195507 corresponding to *Lycopersicon esculentum* zeta-carotene desaturase mRNA (Bartley et al. (1999) "Zeta-carotene desaturase (Accession No. AF195507) from tomato," *Plant Physiol.* 121(4):1383), Accession number X89897 corresponding to *C. annuum* mRNA for zeta-carotene/neurosporene dehydrogenase (Breitenbach et al. (1999) "Catalytic properties of an expressed and purified higher plant type zeta-carotene desaturase from *Capsicum annuum*," *Eur. J. Biochem.* 265(1):376-383), and Accession number AF047490 corresponding to *Zea mays* zeta-carotene desaturase precursor mRNA (Luo et al. (1999) "A Maize cDNA Encoding Zeta Carotene Desaturase (Accession No. AF047490)," *Plant Physiol.* 120(4):1206).

Lycopene β-Cyclases

Examplary lycopene β-cyclase encoding sequences that are optionally utilized to transform pineapple cells or plants according to the methods of the invention include those corresponding to, e.g., Accession number AY094582 corresponding to *Citrus sinensis* lycopene beta-cyclase gene (Xu et al. "Molecular cloning of lycopene beta-cyclase gene from Red flesh navel orange by using Tail-PCR," unpublished), Accession number AF240787 corresponding to *Citrus sinensis* lycopene beta-cyclase gene (Xu et al. "Molecular cloning of lycopene beta-cyclase gene from orange (*Citrus sinensis*)," unpublished), Accession number AF254793 corresponding to *Lycopersicon esculentum* chromoplast-specific lycopene beta-cyclase mRNA (Ronen et al. (2000) "An alternative pathway to beta-carotene formation in plant chromoplasts discovered by map-based cloning of beta and old-gold color mutations in tomato," *Proc. Natl. Acad. Sci. U.S.A.* 97(20):11102-11107), Accession number X86452 corresponding to *L. esculentum* mRNA for lycopene beta-cyclase (Cunningham et al. (1996) "Functional analysis of the beta and epsilon lycopene cyclase enzymes of Arabidopsis reveals a mechanism for control of cyclic carotenoid formation," *Plant Cell* 8(9):1613-1626).

Lycopene ε-cyclases

Lycopene ε-cyclase encoding sequences that are optionally utilized herein include those corresponding to, e.g., Accession number AF486650 corresponding to *Citrus x paradisi* lycopene epsilon-cyclase mRNA (Costa et al. (2002) direct submission to Horticultural Sciences, University of Florida, Gainesville, Fla., USA), Accession number AF463497 corresponding to *Spinacia oleracea* lycopene epsilon-cyclase (lec) mRNA. DeSouza et al. "Production of Lutein in Microorganisms," unpublished), Accession number AF321538 corresponding to *Lactuca saliva* lycopene epsilon-cyclase mRNA (Cunningham et al. (2001) "One ring or two? Determination of ring number in carotenoids by lycopene varepsilon-cyclases," *Proc. Natl. Acad. Sci. U.S.A.* 98(5):2905-2910), and Accession number Y14387 corresponding to *Lycopersicon esculentum* mRNA for lycopene epsilon-cyclase (Ronen et al. "Regulation of expression of the gene for lycopene epsilon cyclase during fruit ripening of tomato," unpublished).

β-Carotene Hydroxylases

Examplary β-carotene hydroxylase encoding sequences that are optionally utilized to transform pineapple cells or plants according to the methods of the invention include those corresponding to, e.g., Accession number AC092389 corresponding to *Oryza sativa* chromosome 10 BAC OSJNBa0053C23 genomic sequence (Buell et al. "*Oryza saliva* chromosome 10 BAC OSJNBa0053C23 genomic sequence," unpublished), Accession number AF499108 corresponding to *Vitis vinifera* beta-carotene hydroxylase (bch1) gene (Young et al. "Isolation, characterization and heterologous expression of a beta-carotene hydroxylase from grapevine (*Vitis vinifera*)," unpublished), Accession number AF315289 corresponding to *Citrus unshiu* beta-carotene hydroxylase (CHX2) mRNA (Kim et al. (2001) "Isolation and characterization of cDNAs encoding beta-carotene hydroxylase in *Citrus*," *Plant Sci.* 161(5):1005-1010), and Accession number AF296158 corresponding to *Citrus unshiu* beta-carotene hydroxylase (CHX1) mRNA (Kim et al. (2001) "Isolation and characterization of cDNAs encoding beta-carotene hydroxylase in *Citrus*," *Plant Sci.* 161(5):1005-1010).

ε-Hydroxylases

Epsilon-hydroxylase encoding sequences that are optionally utilized herein include those corresponding to, e.g., Accession number AE005173 corresponding to *Arabidopsis thaliana* chromosome 1, bottom arm complete sequence (Theologis et al. (2000) "Sequence and analysis of chromosome 1 of the plant *Arabidopsis thaliana*," *Nature* 408(6814):816-820) and Accession number AE005172 corresponding to *Arabidopsis thaliana* chromosome 1, top arm complete sequence. Theologis et al. (2000) "Sequence and analysis of chromosome 1 of the plant *Arabidopsis thaliana*," *Nature* 408(6814):816-820.

In addition, the nucleic acid sequences for carotenoid biosynthetic enzyme clusters from carotenogenic microorganisms can be obtained from GenBank®, such as Accession No. M87280 (*Erwinia herbicola* Eho10), D90087 (*Erwinia uredovora*), U62808 (*Flavobacterium*), D58420 (*Agrobacterium aurantiacum*) and M90698 (*Erwinia herbicola* Eho13).

V. Artificially Evolved Carotenoid Biosynthetic Polypeptides

In certain embodiments of the invention, artificially evolved carotenoid biosynthetic polypeptides are used to modulate carotenoid accumulation in transgenic pineapple cells and plants. For example, any of the exemplary target carotenoid biosynthetic sequences described above can be artificially evolved to acquire desired traits or properties, such as increased catalytic efficiency, increased substrate specificity, and/or the like. A variety of artificial diversity generating procedures are available and described in the art, which can be used to produce artificially evolved carotenoid biosynthetic polypeptides. These procedures can be used separately or in combination to produce variants of a nucleic acid, as well as variants of carotenoid biosynthetic proteins encoded by the nucleic acid variants. Individually and collectively, these procedures provide robust, widely applicable ways of engineering or rapidly evolving individual carotenoid biosynthetic nucleic acids and proteins, or even the entire carotenoid pathway or selected portions of the pathway. The products of these procedures can be used in the transformation methods of the invention.

In particular, the result of any of the diversity generating procedures described herein or otherwise known in the art can be the generation of one or more nucleic acids that are typically selected or screened for nucleic acids encoding carotenoid biosynthetic enzymes with or which confer desirable properties, such as increased catalytic efficiency, etc. This can include identifying any activity that can be detected, for example, in an automated or automatable format, by any of the assays known in the art. A variety of related (or even unrelated) properties can be evaluated, in serial or in parallel, at the discretion of the practitioner.

Artificially evolved carotenoid biosynthetic polypeptides that are optionally used in the transformation methods of the present invention can be derived using many different techniques. To illustrate, chimeric enzymes including identifiable components (e.g., protein domains) derived from two or more parental sequences can be utilized. For example, domains in different phytoene synthases can be identified and selected for inclusion in a chimeric progeny phytoene synthase. Various sequence comparison algorithms and other tools that are useful for chimeric enzyme design are described further below.

Artificially evolved enzymes can additionally be developed using various mutagenic methods, such as cassette mutagenesis, site-directed mutagenesis (see, e.g., Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)), chemical mutagenesis, error-prone PCR, site-saturation mutagenesis, recursive ensemble mutagenesis, and the like. To illustrate, error-prone PCR can be used to generate nucleic acid variants. Using error-prone PCR, for example, PCR is performed under conditions where the copying fidelity of the DNA polymerase is low, such that a high rate of point mutations is obtained along the entire length of the PCR product. Examples of such techniques are described further in, e.g., in Leung et al. (1989) *Technique* 1:11-15 and Caldwell et al. (1992) *PCR Methods Applic.* 2:28-33. To further illustrate an exemplary mutagenic technique, cassette mutagenesis is optionally used in a process that replaces a small region of a double stranded DNA molecule with, e.g., a synthetic oligonucleotide cassette that differs from the native sequence. The synthetic oligonucleotide can contain, e.g., completely and/or partially randomized native sequence(s). Additional details relating to cassette mutagenesis are described in, e.g., Wells et al. (1985) "Cassette mutagenesis: an efficient method for generation of multiple mutations at defined sites" *Gene* 34:315-323. Another exemplary method of creating molecular diversity mutagenically is a recursive ensemble mutagenesis process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin et al. (1992) *Proc. Natl. Acad. Sci. USA* 89:7811-7815. The mutagenic techniques referred to above are provided simply to illustrate certain procedures that are optionally used to produce diversity in nucleic acids that encode carotenoid biosynthetic polypeptides. Many other approaches to creating diversity via mutagenesis are well-known and are also suitable for the methods of the present invention.

Nucleic acids that encode carotenoid biosynthetic polypeptides, such as those described above, are also optionally used as substrates for a variety of recombination reactions, such as a recursive sequence recombination protocol. Many of these techniques are described in various publications including, e.g., Chang et al. (1999) "evolution of a cytokine using DNA family shuffling" *Nature Biotechnology* 17:793-797, Crameri et al. (1998) "DNA shuffling of a family of genes from diverse species accelerates directed evolution" *Nature* 391:288-291, Crameri et al. (1997) "Molecular evolution of an arsenate detoxification pathway by DNA shuffling," *Nature Biotechnology* 15:436438, Crameri et al. (1996) "Improved green fluorescent protein by molecular evolution using DNA shuffling" *Nature Biotechnology* 14:315-319, Stemmer (1995) "Searching Sequence Space" *Bio/Technology* 13:549-553, and Stemmer (1994) "Rapid evolution of a protein in vitro by DNA shuffling" *Nature* 370:389-391.

Many of the diversity generating procedures described above (e.g., chimeric enzyme design and synthesis, recursive sequence recombination, etc.), include determining levels of homology among starting sequences. For example, in the processes of sequence comparison and homology determination, one sequence, e.g., one fragment or subsequence of a gene sequence to be recombined, can be used as a reference against which other test nucleic acid sequences are compared. This comparison can be accomplished with the aid of a sequence comparison algorithm or by visual inspection. When an algorithm is employed, test and reference sequences are input into a computer, subsequence coordinates are designated, as necessary, and sequence algorithm program parameters are specified. The algorithm then calculates the percent sequence identity for the test nucleic acid sequence(s) relative to the reference sequence, based on the specified program parameters.

For purposes of the present invention, suitable sequence comparisons can be executed, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection. See generally, *Current Protocols in Molecular Biology*, F. M. Ausubel et al., eds., Current Protocols, a joint venture between Greene Publishing Associates, Inc. and John Wiley & Sons, Inc., (supplemented through 2001). Another example search algorithm that is suitable for determining percent sequence identity and sequence similarity is the Basic Local Alignment Search Tool (BLAST) algorithm, which is described in, e.g., Altschul et al. (1990) *J. Mol. Biol.* 215:403-410. Software for performing BLAST analyses is publicly available through the National Center for Biotechnology Information on the world wide web at ncbi.nlm.nih.gov.

Kits for mutagenesis, library construction and other diversity generation methods are commercially available. For example, kits are available from, e.g., Stratagene (e.g., QuickChange™ site-directed mutagenesis kit, and Chameleon™ double-stranded, site-directed mutagenesis kit), Bio/Can Scientific, Bio-Rad (e.g., using the Kunkel method referred to above), Boehringer Mannheim Corp., Clonetech Laboratories, DNA Technologies, Epicentre Technologies (e.g., 5 prime 3 prime kit), Genpak Inc., Lemargo Inc., Life Technologies (Gibco BRL), New England Biolabs, Pharmacia Biotech, Promega Corp., Quantum Biotechnologies, Amersham International plc, and Anglian Biotechnology Ltd.

VI. Nucleic Acid Preparation

Nucleic acid segments that encode carotenoid biosynthetic polypeptides, such as those described above, can be prepared using various methods or combinations thereof, including certain DNA synthetic techniques, DNA amplification, nuclease digestion, etc. Searchable sequence information that is available from nucleic acid databases can be utilized during nucleic acid segment and vector selection and/or design processes. Genbank®, Entrez®, EMBL, DDBJ, GSDB, NDB and the NCBI are examples of public database/search services that can be accessed. These databases are generally available via the internet or on a contract basis from a variety of companies specializing in genomic information generation and/or storage. These and other helpful resources are readily available and known to those of skill.

The sequence of a polynucleotide to be used in any of the methods of the present invention can also be readily determined using techniques well-known to those of skill, including Maxam-Gilbert, Sanger Dideoxy, and Sequencing by Hybridization methods. For general descriptions of these processes consult, e.g., Stryer, *Biochemistry* 4$^{th}$ Ed., W.H. Freeman and Company (1995) and Lewin, *Genes VI*, Oxford University Press (1997). See also, Maxam and Gilbert (1977) "A New Method for Sequencing DNA," *Proc. Natl. Acad. Sci.* 74:560-564, Sanger et al. (1977) "DNA Sequencing with Chain-Terminating Inhibitors," *Proc. Natl. Acad. Sci.* 74:5463-5467, Hunkapiller et al. (1991) "Large-Scale and Automated DNA Sequence Determination," *Science* 254:59-67, and Pease et al. (1994) "Light-Generated Oligonucleotide Arrays for Rapid DNA Sequence Analysis," *Proc. Natl. Acad. Sci.* 91:5022-5026.

Nucleic acid segments that encode the carotenoid biosynthetic enzymes described above can be synthesized by chemical techniques, for example, utilizing the phosphotriester method of Matteucci et al. (1981) *J. Am. Chem. Soc.,* 103: 3185. Of course, by chemically synthesizing the coding sequence, any desired modifications can be made simply by substituting the appropriate bases for those encoding the native amino acid residue sequence. However, nucleic acid segments including sequences discussed previously are typically preferred. Furthermore, nucleic acid segments encoding carotenoid biosynthetic enzymes are optionally obtained from existing recombinant DNA molecules (plasmid vectors) containing those genes. Certain of these plasmids are available from the American Type Culture Collection (ATCC), 12301 Parklawn Drive, Rockville, Md., 20852.

The nucleic acid segments and constructs or vectors of the present invention can be prepared by a number of techniques known in the art, such as molecular cloning techniques. A wide variety of cloning and in vitro amplification methods suitable for the construction of recombinant nucleic acids, such as expression vectors, are well-known to persons of skill. Vectors suitable for use in the present invention are described further below. General texts which describe molecular biological techniques useful herein, including mutagenesis, include Berger and Kimmel, *Guide to Molecular Cloning Techniques. Methods in Enzymology*, Vol. 152, Academic Press, Inc. (1999)("Berger"); Sambrook et al., *Molecular Cloning—A Laboratory Manual* 2nd Ed., Vol. 1-3, Cold Spring Harbor Laboratory (2000) ("Sambrook"); and *Current Protocols in Molecular Biology*, Ausubel et al. (Eds.), Current Protocols, a joint venture between Greene Publishing Associates, Inc. and John Wiley & Sons, Inc., (supplemented through 2000) ("Ausubel"). Examples of techniques sufficient to direct persons of skill through in vitro amplification methods, including the polymerase chain reaction (PCR), the ligase chain reaction (LCR), Qβ-replicase amplification and other RNA polymerase mediated techniques (e.g., NASBA) are found in Berger, Sambrook, and Ausubel, as well as Mullis et al. (1987) U.S. Pat. No. 4,683, 202; *PCR Protocols A Guide to Methods and Applications* (Innis et al., eds.), Academic Press Inc. (1990)("Innis"); Arnheim & Levinson (1990) *Chemical and Engineering News* 36-47; Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al., (1988) *Science* 241:1077-1080; Van Brunt (1990) *Biotechnology* 8:291-294; Wu and Wallace, (1989) *Gene* 4:560; Barringer et al. (1990) *Gene* 89:117, and Sooknanan and Malek (1995) *Biotechnology* 13:563-564. Additional methods of cloning in vitro amplified nucleic acids are also described in U.S. Pat. No. 5,426,039 to Wallace et al. Methods of amplifying large nucleic acids by PCR are summarized in Cheng et al. (1994) *Nature* 369:684-685 and the references cited therein, in which PCR amplicons of up to 40 kb are generated. One of skill will also appreciate that essentially any RNA can be converted into a double stranded DNA suitable for restriction digestion, PCR expansion and sequencing using reverse transcriptase and a polymerase. See, Ausubel, Sambrook and Berger, all supra.

The isolation of a nucleic acid sequence for inclusion in a vector construct of the invention may be accomplished by any number of techniques known in the art. For instance, oligonucleotide probes based on known sequences can be used to identify the desired gene in a cDNA or genomic DNA library. Probes may be used to hybridize with genomic DNA or cDNA sequences to isolate homologous genes in the same or different species. Alternatively, antibodies raised against an enzyme can be used to screen an mRNA expression library for the corresponding coding sequence.

Alternatively, the nucleic acids of interest (e.g., genes encoding carotenoid biosynthetic polypeptides) can be amplified from nucleic acid samples using amplification techniques. For instance, polymerase chain reaction (PCR) technology can be used to amplify the sequences of desired genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see Innis, supra.

Polynucleotides may also be synthesized by well-known techniques as described in the technical literature. See, e.g., Carruthers et al. (1982) *Cold Spring Harbor Symp. Quant. Biol.* 47:411-418, and Adams et al. (1983) *J. Am. Chem. Soc.* 105:661. Double stranded DNA segments may then be obtained either by synthesizing the complementary strand and annealing the strands together under appropriate conditions, or by adding the complementary strand using DNA polymerase with an appropriate primer sequence.

Oligonucleotides for use as probes, e.g., in in vitro amplification methods, for use as gene probes are typically synthesized chemically according to the solid phase phosphoramidite triester method described by Beaucage and Caruthers (1981) *Tetrahedron Letts.* 22(20):1859-1862, e.g., using an automated synthesizer, as described in Needham-VanDevanter et al. (1984) *Nucleic Acids Res.* 12:6159-6168. Oligonucleotides for use in the nucleic acid constructs or vectors of the present invention can also be custom made and ordered from a variety of commercial sources known to persons of skill.

VII. Vectors

Essentially any vector or vector system can be used to create the transformed pineapple cells and plants of the invention. In some embodiments, nucleic acid segments that encode carotenoid biosynthetic polypeptides are operatively linked to vectors in the form of plasmids or plasmid systems (e.g., a binary system, a trinary system, shuttle vector system, etc.). Certain exemplary plasmid systems that are optionally adapted for use in the present invention are described in, e.g., U.S. Pat. No. 5,977,439 to Hamilton (issued Nov. 2, 1999), U.S. Pat. No. 5,929,306 to Torisky et al. (issued Jul. 27, 1999), U.S. Pat. No. 5,149,645 to Hoekema et al. (issued Sep. 22, 1992), U.S. Pat. No. 6,165,780 to Kawasaki (issued Dec. 26, 2000), U.S. Pat. No. 6,147,278 to Rogers et al. (issued Nov. 14, 2000), U.S. Pat. No. 4,762,785 to Comai (issued Aug. 9, 1988), and U.S. Pat. No. 5,068,193 to Comai (issued Nov. 26, 1991).

The nucleic acid segments described herein, e.g., in the form of expression cassettes typically include the in 5'-3' direction of transcription, a transcriptional and translational initiation region, a DNA sequence of interest (e.g., a gene encoding a carotenoid biosynthetic polypeptide), and a transcriptional and translational termination region functional in pineapple plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991), *Mol. Gen. Genet.*, 262:141-144; Proudfoot, (1991), *Cell,* 64:671-674; Sanfacon et al., (1991), *Genes Dev.,* 5:141-149; Mogen et al., (1990), *Plant Cell,* 2:1261-1272; Munroe et al., (1990), *Gene,* 91:151-158; Ballas et al., (1989), *Nucleic Acids Res.,* 17:7891-7903; and Joshi et al., (1987), *Nucleic Acid Res.,* 15:9627-9639).

In certain embodiments, the carotenoid biosynthetic genes of the present invention will be targeted to plastids, such as chloroplasts, for expression. In this manner, where the carotenoid biosynthetic gene is not directly inserted into the plastid, the expression cassette will additionally contain a gene encoding a transit peptide to direct the gene of interest to the plastid. Such transit peptides are known in the art. See, e.g., Von Heijne et al. (1991) *Plant Mol. Biol. Rep.* 9:104-126; Clark et al. (1989) *J. Biol Chem.* 264:17544-17550; della-Cioppa et al. (1987) *Plant Physiol.* 84:965-968; Romer et al. (1993) *Biochem. Biophys. Res Commun.* 196:1414-1421; and, Shah et al. (1986). *Science* 233:478-481. Plant carotenoid genes useful in the invention may utilize native or heterologous transit peptides.

The constructs of the invention may also include any other necessary regulators such as plant translational consensus sequences (Joshi, C. P., (1987), *Nucleic Acids Research,* 15:6643-6653), introns (Luehrsen and Walbot, (1991), *Mol. Gen. Genet.,* 225:81-93) and the like, operably linked to the nucleotide sequence of interest.

In some embodiments, 5' leader sequences are included in the expression cassette construct. Such leader sequences can act to enhance translation. Translation leaders are known in the art and include: *picornavirus* leaders, for example, EMCV leader (*Encephalomyocarditis* 5' noncoding region) (Elroy-Stein et al. (1989) *PNAS USA* 86:6126-6130); *potyvirus* leaders, for example, TEV leader (Tobacco Etch Virus) (Allison et al., (1986); MDMV leader (Maize Dwarf Mosaic Virus); Virology, 154:9-20), and human immunoglobulin heavy-chain binding protein (BiP), (Macejak, D. G., and Sarnow, P., (1991), *Nature,* 353:90-94; untranslated leader from the coat protein mRNA of alfalfa mosaic virus (AMV RNA 4), (Jobling, S. A., and Gehrke, L., (1987), *Nature,* 325:622-625; tobacco mosaic virus leader (TMV), (Gallie, D. R. et al., (1989), *Molecular Biology of RNA,* pages 237-256; and maize chlorotic mottle virus leader (MCMV) (Lommel, S. A. et al., (1991), *Virology,* 81:382-385. See also, Della-Cioppa et al., (1987), *Plant Physiology,* 84:965-968.

Depending upon where the DNA sequence of interest is to be expressed, it may be desirable to synthesize the sequence with pineapple plant preferred codons, or alternatively with chloroplast preferred codons. Pineapple plant preferred codons may be determined from the codons of highest frequency in the proteins expressed in the largest amount in the particular plant species of interest. See, European Patent Application Nos. 0359472 and 0385962; International Application No. WO 91/16432; Perlak et al. (1991) *Proc. Natl. Acad. Sci. USA* 88:3324-3328; and Murray et al. (1989) *Nucleic Acids Res.* 17: 477-498. In this manner, the nucleotide sequences can be optimized for expression in pineapple plants. It is recognized that all or any part of the gene sequence may be optimized or synthetic. That is, synthetic or partially optimized sequences may also be used. For the construction of chloroplast preferred genes, see e.g., U.S. Pat. No. 5,545,817.

In preparing expression cassettes, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g., transitions and transversions, may be involved.

The vectors of the invention also typically include expression control elements, such as promoters. Carotenoid biosynthetic polypeptide coding genes are operatively linked to the expression vector to permit the promoter sequence to direct RNA polymerase binding and expression of the polypeptide coding gene. Useful in expressing the polypeptide coding gene are promoters which are inducible, viral, synthetic, constitutive as described in, e.g., Poszkowski et al. (1989) *EMBO J*. 3:2719 and Odell et al. (1985) *Nature* 313:810 (1985), and temporally regulated, spatially regulated, and spatiotemporally regulated as described in, e.g., Chua et al. (1989) *Science* 244:174-181.

The choice of which expression vector and, e.g., to which preselected organ-enhanced promoter a polypeptide coding gene is operatively linked depends on the functional properties desired, e.g., the location and timing of protein expression. A vector that is useful in practicing the present invention integrates into the genome of pineapple plants, is capable of directing the replication, and also the expression of the carotenoid biosynthetic polypeptide coding gene included in the nucleic acid segment to which it is operatively linked. It is well known in the art that the entire expression vector does not integrate into the host plant genome, but only a portion integrates. Nonetheless, the vector will be said to integrate for ease of expression.

In some embodiments of the present invention, the constructs include elements in addition to the conjoined nucleic acid sequences, such as promoters, enhancer elements, and signaling sequences. Exemplary promoters include the CaMV promoter, a promoter from the ribulose-1,5-bisphosphate carboxylase-oxygenase small subunit gene, a ubiquitin promoter, and a rolD promoter. Exemplary enhancer elements are described in, e.g., U.S. Pat. No. 6,271,444, which issued Aug. 7, 2001 to McBride et al. Exemplary signaling sequences include, but are not limited to, nucleic acid sequences encoding tissue-specific transit peptides, such as chloroplast transit peptides (see, e.g., Zhang et al. (2002) *Trends Plant Sci* 7(1):14-21).

In certain embodiments, a strongly or weakly constitutive plant promoter can be employed which will direct expression of the encoded sequences in all tissues of a pineapple plant. Such promoters are active under most environmental conditions and states of development or cell differentiation. Examples of constitutive promoters include the 1' or 2'derived from T-DNA of *Agrobacterium tumefaciens*, and other transcription initiation regions from various plant genes known to those of skill. In situations in which overexpression of a gene is undesirable, a weak constitutive promoters can be used for lower levels of expression. In instances where high levels of expression are sought, a strong promoter, e.g., a t-RNA or other pol III promoter, or a strong pol II promoter, such as the cauliflower mosaic virus promoter, can be used.

Alternatively, a plant promoter may be under environmental control. Such promoters are referred to here as "inducible" promoters. Examples of environmental conditions that may effect transcription by inducible promoters include pathogen attack, anaerobic conditions, or the presence of light.

In some embodiments, the promoters incorporated into the constructs of the present invention are "tissue-specific" and, as such, under developmental control in that the desired gene is expressed only in certain tissues, such as fruit-tissues. In embodiments in which one or more nucleic acid sequences endogenous to the pineapple plant are incorporated into the construct, the endogenous promoters (or variants thereof) from these genes can be employed for directing expression of the genes in the transfected plant. Tissue-specific promoters can also be used to direct expression of heterologous structural genes, including the artificially evolved nucleic acids described herein.

In addition to the promoters noted above, promoters of bacterial origin which operate in plants include the octopine synthase promoter, the nopaline synthase promoter and other promoters derived from native Ti plasmids (see, Herrara-Estrella et al. (1983) *Nature* 303:209-213). Viral promoters include the 35S and 19S RNA promoters of cauliflower mosaic virus (Odell et al. (1985) *Nature* 313:810-812). Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J*. 7:3315-3327.

In preparing the constructs of the invention, sequences other than the promoter and the conjoined nucleic acid segment can also be employed. If normal polypeptide expression is desired, a polyadenylation region at the 3'-end of the coding region can be included. The polyadenylation region can be derived from the natural gene, from a variety of other plant genes, or from T-DNA.

Typical vectors useful for expression of genes in pineapple plants are well known in the art and include vectors derived from the tumor-inducing (Ti) plasmid of *Agrobacterium tumefaciens* described by Rogers et al. (1987) *Meth. in Enzymol.*, 153:253-277 (1987). These vectors are plant integrating vectors in that on transformation, the vectors integrate a portion of vector DNA into the genome of the pineapple plant. For integrating vectors based on the Ti plasmid, the region integrated into the host plant chromosomes is that between the right and left borders of the Ti plasmid.

Exemplary *A. tumefaciens* vectors useful herein are plasmids pKYLX6 and pKYLX7 of Schardl et al. (1987) *Gene* 61:1-11 and Berger et al. (1989) *Proc. Natl. Acad. Sci. U.S.A.*, 86:8402-8406. Plasmid pKYLX6 is an *E. coli* vector designed for intermediate constructs, whereas plasmid pKYLX7 is an *A. tumefaciens* vector designed for integration of cloned genes. Modified vectors pKYLX61 and pKYLX71 contain HindIII, XhoI, BamHI, PstI and SstI sites in place of the original HindIII-SstI fragment multiple cloning site region. Another useful vector herein is plasmid pBI101.2 that is available from Clontech Laboratories, Inc., Palo Alto, Calif. Plasmids pKYLX7, pKYLX71 and pB7101.2 are binary vectors that are used in *A. tumefaciens* with another vector having a vir gene. Other vectors systems are also optionally utilized herein including, e.g., trinary vector systems. Another plant transformation system is based on *Agrobacterium rhizogenes* that induces hairy roots rather than a tumor on transformation. See, e.g., International Publication No. WO 88/02405 (published Apr. 7, 1988) describes the use of *A. rhizogenes* strain A4 and its Ri plasmid along with *A*.

*tumefaciens* vectors pARC8 or pARC16 to transform plants. *Agrobacterium*-mediated transformation is described further below.

The use of retroviral expression vectors is also contemplated. As used herein, the term "retroviral expression vector" refers to a DNA molecule that includes a promoter sequence derived from the long terminal repeat (LTR) region of a retrovirus genome. Because some of the carotenoid products of the invention are associated with food production and coloration, the retroviral expression vector is preferably replication-incompetent in eukaryotic cells. The construction and use of retroviral vectors has been described by, e.g., Verma in International Publication No. WO 87/00551, and in Cocking et al. (1987) *Science* 236:1259-62.

In some embodiments, the vector used to express the carotenoid biosynthetic polypeptide coding gene includes a plant selectable marker that confers a selectable phenotype on the transformed pineapple cell. The selectable plant marker gene on the DNA segment to be inserted will usually encode a function which permits the survival and emergence of transformed embryogenic or organogenic tissue or callus in a selective medium. Usually, the selectable marker gene will encode antibiotic resistance, with suitable genes including those coding for resistance to the antibiotic spectinomycin (e.g., the aadA gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron. Selection based on resistance to sulfonylurea-type herbicides is preferred. Selectable markers based on the green fluorescent protein (GFP) or β-glucuronidase (GUS) are also optionally used and are described further in, e.g., Mantis et al. (2000) "Comparing the utility of β-glucuronidase and green fluorescent protein for detection of weak promoter activity in *Arabidopsis thaliana*," *Plant Molecular Biology Reporter* 18:319-330.

Methods to select transformed plant cells incorporating a desired resistance gene are well known in the art. For example, if the marker is sulfonylurea resistance, the selection medium generally contains a sulfonylurea-type herbicide at an appropriate concentration (e.g., chlorsulfuron in the range of 1-1000 µg/l, preferably about 5-100 µg/l). For selection of geneticin resistant pineapple cells or tissue which contain the NPTII gene, geneticin is typically included in the medium at 10-50 mg/l. Spectinomycin resistance cells or tissue containing the aadA gene are typically selected on medium containing 200-1000 mg/l spectinomycin.

Since many carotenoids are colored, these carotenoid products can be visualized and determined by their characteristic spectra and other analytic methods. Therefore, genes encoding carotenoid biosynthetic enzymes may be used as marker genes to allow for visual selection of transformants. In particular, such transformed cells generally display colors ranging from yellow to orange to red as a result of the increased carotenoid levels. In some embodiments, other analytical techniques can be used to select transformed pineapple cells including, e.g., mass spectrometry, thin layer chromatography (TLC), high pressure liquid chromatography (HPLC), capillary electrophoresis (CE), NMR spectroscopy, and conventional hybridization techniques.

A variety of methods have been developed to operatively link DNA to vectors via complementary cohesive termini or blunt ends. For instance, complementary homopolymer tracts can be added to the nucleic acid segment to be inserted and to the vector. The vector and nucleic acid segment are then joined by hydrogen bonding between the complementary homopolymeric tails to form recombinant DNA molecules.

Alternatively, synthetic linkers that include one or more restriction endonuclease sites can be used to join the nucleic acid segment to the integrating expression vector. The synthetic linkers are attached to blunt-ended nucleic acid segments by incubating the blunt-ended nucleic acid segments with a large excess of synthetic linker molecules in the presence of an enzyme that is able to catalyze the ligation of blunt-ended nucleic acid molecules, such as bacteriophage T4 DNA ligase. Thus, the products of the reaction are nucleic acid segments carrying synthetic linker sequences at their ends. These nucleic acid segments are then cleaved with the appropriate restriction endonuclease and ligated into an integrating expression vector that has been cleaved with an enzyme that produces termini compatible with those of the synthetic linker. Synthetic linkers containing a variety of restriction endonuclease sites are commercially available from a number of sources including New England BioLabs (Beverly, Mass.).

The introduced DNA segments may additionally contain one or more genes that are chosen to provide new pineapple plant traits, to enhance an existing pineapple plant trait, or to otherwise modify expression of phenotypes exhibited by the pineapple plant, that is, in addition to modifying carotenoid levels in pineapple plants. Such additional traits include herbicide resistance, pesticide resistance, disease resistance, environmental tolerance (e.g., heat, cold, drought, salinity), morphology, growth characteristics, nutritional content, taste, yield, horticultural characteristics, consumer (quality) traits, and the like. Examples of genes that can be introduced include those to confer resistance or to reduce susceptibility to particular diseases or pests of pineapple. Examples include those reducing susceptibility to Fusariosis, mealy bug wilt, marbling disease, and nematodes.

VIII. Carotenoid Biosysthesis Modulation Strategies

Functional genes to be introduced may be structural genes which encode polypeptides that impart the desired phenotype, such as modified pineapple fruit coloration. Alternatively, functional genes may be regulatory genes that play roles in transcriptional and/or translational control to suppress, enhance, or otherwise modify the transcription and/or expression of endogenous genes within the pineapple plants. In some embodiments, for example, introduced carotenoid biosynthetic polypeptide expression regulators are nucleic acid segments that encode carotenoid biosynthetic polypeptide transcription factors, which when expressed in transformed cells effect elevated expression of targeted carotenoid biosynthetic genes. In other embodiments, carotenoid biosynthetic polypeptide expression regulators include nucleic acid segments that encode carotenoid biosynthetic polypeptide promoters and/or carotenoid biosynthetic polypeptide enhancers, which nucleic acid segments homologously recombine with promoters and/or enhancers of endogenous carotenoid biosynthetic polypeptide genes to increase or decrease expression of the genes as desired.

To further illustrate, various DNA constructs can be used in a number of techniques to suppress expression of endogenous plant genes, e.g., sense or antisense suppression or ribozymes. Anti-sense RNA inhibition of gene expression has been shown; see, e.g., Sheehy et al. (1988) *Proc. Nat. Acad. Sci. USA* 85:8805-8809, and Hiatt et al. U.S. Pat. No. 4,801, 340. For examples of the use of sense suppression to modulate expression of endogenous genes see, Napoli et al. (1990) *The Plant Cell* 2:279-289, and U.S. Pat. No. 5,034,323.

Catalytic RNA molecules or ribozymes can also be used to inhibit gene expression, which is optionally used to effect the accumulation of selected carotenoids that are upstream in the carotenoid biosynthetic pathway from the gene that is inhibited. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus, and subterranean clover mottle virus. The design and use of target RNA-specific ribozymes is described in Haseloff et al. (1988) *Nature* 334:585-591.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of noncoding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

To further illustrate, RNA interference (RNAi), also known as Post-Transcriptional Gene Silencing (PTGS), is also optionally utilized to modulate carotenoid accumulation in pineapple cells and plants. RNAi is a cellular mechanism that selectively negates the effect of a target gene by destroying messenger RNA. By destroying the targeted mRNA, protein synthesis is interrupted, thereby effectively "silencing" the target gene. In certain embodiments, this process is initiated by double-stranded RNA (dsRNA), where one strand is substantially identical to the target mRNA sequence. Accordingly, in some embodiments of the invention, carotenoid biosynthetic polypeptide expression regulators comprise nucleic acid segments that are introduced into pineapple cells to trigger the production of double stranded dsRNA, which is then cleaved into small interfering RNA (siRNA) as part of an RNAi process. This results in the destruction of the target mRNA, thereby effectively silencing expression of a target gene, such as an endogenous gene encoding a carotenoid biosynthetic polypeptide. Additional details relating to RNAi are described in, e.g., U.S. Pat. No. 6,573,099, entitled "GENETIC CONSTRUCTS FOR DELAYING OR REPRESSING THE EXPRESSION OF A TARGET GENE," which issued Jun. 3, 2003 to Graham, and in, e.g., Arenz et al. (2003) "RNA interference: from an ancient mechanism to a state of the art therapeutic application?" *Naturwissenschaften.* 90(8):345-59, Wang et al. (2003) "RNA interference: antiviral weapon and beyond," *World J Gastroenterol.* 9(8):1657-61, and Lavery et al. (2003) "Antisense and RNAi: powerful tools in drug target discovery and validation" *Curr Opin Drug Discov Devel.* 6(4):561-9. Custom nucleic acid segments that can be utilized to effect target gene silencing are also commercially available from various suppliers, such as Ambion, Inc. (Austin, Tex., USA), Benitec Australia Limited (St Lucia, AU), and the like.

Often the functional genes to be introduced will be modified from their native form. For example, sense and anti-sense constructs referred to above often have all or a portion of the transcript of the native gene operably linked to a promoter sequence at the 5' end of the transcribable segment, and operably linked to the 3+ sequence of another gene (including polyadenylation sequences) at the 3' end of the transcribable segment. As is apparent to those skilled in the art, the promoter sequence could be one of the many plant active sequences already described. Alternatively, other plant-active promoter sequences could be derived specifically to be linked to the transcribable segment. The promoter can be endogenous to pineapple, or can be from an exogenous source such as a cauliflower mosaic virus 35S promoter (Odell et al. (1985) *Nature* 313:810-812), the ubiquitin 1 promoter (Christiensen et al. (1992) *Plant Mol. Biol.* 18:675-689), or the Smas promoter (Ni et al. (1995) *Plant J.* 7:661-676). The 3' end sequence to be added can be derived from, preferably, the nopaline synthase or octopine synthase genes, or alternatively from another plant gene, or less preferably from any other eukaryotic gene.

As described above, the production of carotenoids can be elevated in pineapple cells and plants transformed with nucleic acid segments (e.g., a first gene of interest) that, e.g., encode carotenoid biosynthetic enzymes. Optionally, once this biosynthetic activity has been increased by expression of these introduced carotenoid biosynthesis genes, the pathway can be diverted for the production and accumulation of specific carotenoids. The diversion typically includes the use of at least one second gene of interest. To illustrate, the second gene can encode an enzyme to force the production of a particular carotenoid or alternatively can encode a gene to stop the pathway for the accumulation of a particular carotenoid. To force the production of a particular carotenoid, expression of a carotenoid biosynthesis gene in the pathway for the desired carotenoid is used. Genes native or exogenous to the target pineapple plant are optionally used in these methods, including, e.g., carotenoid biosynthesis genes from sources other than plants, such as bacteria, including *Erwinia* and *Rhodobacter* species. Exemplary carotenoid biosynthesis genes that can be utilized for these purposes are described further above. To stop the pathway in order to accumulate a particular carotenoid compound, the second gene will provide for inhibition of transcription of a gene (e.g., native or exogenous) to the target plant in which the enzyme encoded by the inhibited gene is capable of modifying the desired carotenoid compound. Inhibition may be achieved by transcription of the gene to be inhibited in either the sense (cosuppression) or antisense orientation of the gene. Other sense and antisense strategies for modulating carotenoid accumulation in pineapple plants are referred to above.

To further illustrate, to alter the carotenoid composition of a pineapple plant towards the accumulation of higher levels of β-carotene derived carotenoids, such as zeaxanthin, zeaxanthin diglucoside, canthaxanthin, and astaxanthin, inhibition of lycopene ε-cyclase can be achieved to prevent accumulation of α-carotene and other carotenoids that are derivative from α-carotene, such as lutein. In addition to the inhibition of lycopene ε-cyclase, increased expression of a second gene may be utilized for increased accumulation of a particular β-carotene derived carotenoid. For example, increased β-carotene hydroxylase expression is useful for production of zeaxanthin, whereas increased β-carotene hydroxylase and keto-introducing enzyme expression is useful for production of astaxanthin. Alternatively, to accumulate lycopene, the inhibition of lycopene β-cyclase or of lycopene ε-cyclase and lycopene β-cyclase can be effected to reduce conversion of lycopene to α- and β-carotene.

A variety of genes are optionally used as to divert carotenoid biosynthesis in pineapple cells and plants as desired. These include, but are not limited to, β-carotene hydroxylase or crtZ (Hundle et al. (1993) *FEBS Lett.* 315:329-334, Accession No. M87280) for the production of zeaxanthin; genes encoding keto-introducing enzymes, such ascrtW (Misawa et al. (1995) *J. Bacteriol.* 177:6575-6584, WO 95/18220, WO 96/06172) or β-C-4-oxygenzse (crtO; Harker et al. (1997) *FEBS Lett.* 404:129-134) for the production of canthaxanthin; crtZ and crtW or crtO for the production of astaxanthin; ε-cyclase and ε-hydroxylase for the production of lutein; ε-hydroxylase and crtZ for the production of lutein and zeaxanthin; antisense lycopene ε-cyclase (Accession No. U50738) for increased production of β-carotene; antisense lycopene ε-cyclase and lycopene β-cyclase (Hugueney et al. (1995) *Plant J.* 8:417-424, Cunningham Jr et al. (1996) *Plant Cell* 8:1613-1626, Scolnik et al. (1995) *Plant Physiol.* 108: 1343, Accession Nos. X86452, L40176, X81787, U50739 and X74599) for the production of lycopene; antisense plant phytoene desaturase for the production of phytoene; and the like.

In this manner, the pathway can be modified for the high production of any particular carotenoid compound of interest. Such compounds include, but are not limited to, α-cryptoxanthin, β-cryptoxanthin, ζ-carotene, phytofluene, neurosporane, etc. Using the methods of the invention, any compound of interest in the carotenoid pathway can be produced at high levels in selected storage organs, such as the fruit of pineapple plants.

Optionally, the pathway can also be manipulated to decrease levels of a particular carotenoid by, e.g., transforming the pineapple cell with antisense DNA sequences which prevents the conversion of the precursor compound into the particular carotenoid being regulated.

Any strategy for producing a pineapple plant that includes, e.g., a first gene interest, or both first and second genes of interest are optionally utilized in the present invention. For example, a second gene of interest can be used to transform a pineapple plant at the same time as the first gene of interest is introduced (cotransformation). Optionally, the second gene of interest can be introduced into a pineapple plant that has already been transformed with a first gene of interest, or alternatively, transformed pineapple plants, one expressing the first gene of interest and one expressing the second gene of interest, can be crossed to produce progeny having both genes.

IX. Pineapple Explant Sources

Essentially any pineapple variety may be transformed according to the methods described herein. In some embodiments, pineapple explant material is obtained from varieties that are typically used for human consumption, including those of the Smooth Cayenne group, the Spanish group (e.g., Red Spanish), the Perolera group, the Pernambuco group, and the Primavera group. The most important variety for use in the production of canned pineapple, other processed pineapple products, and fresh pineapple is Smooth Cayenne. Within many of these varieties there are a large number of clones which have been established in different geographical areas, and which are adapted to production in those locations. Among the Smooth Cayenne clones are the Champaka clones which have been used extensively for production of canned and fresh pineapple.

The initial explant can be any meristematic region of a plant, including either the main or axillary meristems (apices) of the plant prior to flower formation, and the main or axillary meristems of the crown of the fruit. These regions can be excised from the plant and sterilized by standard methods as described herein and well known to those of ordinary skill to establish sterile cultures in an artificial medium. Such cultures can be maintained for an extended period of time (e.g., weeks, months or years) by a series of propagation steps. Suitable media for establishment and maintenance of in vitro shoot cultures are described in, e.g., DeWald et al. (1988) *Plant Cell Reports*, 7:535-537; Wakasa et al. (1978) *Japan J Breed* 28:113-121; Mathews and Rangan (1981) *Scientia Hort* 14: 227-234; Srinivasa et al. (1981) *Scientia Hort* 15: 23S-238; Fitchet (1990) *Acta Hort* 275: 267-274; Bordoloi and Sarma (1993) *J Assam Science Society* 35: 41-45; and Firoozabady and Moy (2003) "Regeneration of pineapple plants via somatic embryogenesis and organogenesis," In Vitro in press.

In certain embodiments of the present invention, the pineapple cells which are the target for DNA delivery are first obtained from the basal portion of leaves (i.e., leaf base) or sections of the stem of pineapple shoots grown in vitro, and proliferated in culture prior to the DNA delivery step. As used herein, the term "leaf base" refers to that portion of the leaf that is connected to the stem of a shoot of pineapple.

For induction of embryogenic callus or tissue, or organogenic callus or tissue, sterile explants such as leaves or leaf bases are transferred onto specific artificial media that include selected combinations of synthetic plant hormones, which may include, e.g., auxins, cytokinins, gibberellins, and abscisic acid. To illustrate, synthetic auxins are typically selected from, e.g., picloram(4-amino-3,5,6-trichloro-2-pyridinecarboxylic acid), dicamba(3,6-dichloro-2-methoxybenzoic acid), 2,4-D (2,4-dichlorophenoxyacetic acid), indole-3-acetic acid (IAA), indole butyric acid (IBA), NAA (2-naphthalene acetic acid), NOA (naphthoxyacetic acid), or the like. Exemplary cytokinins that can be used include, but are not limited to, BA (benzyl adenine), BAP (benzyl aminopurine), TDZ (thidiazuron), zeatin, kinetin, or the like. Embryogenic and organogenic cell cultures are well-known in the art. For example, additional details relating to somatic embryogenic cell culture and other aspects that are adapted for use in the methods of the present invention are provided in, e.g., U.S. Pat. No. 5,952,543, entitled "GENETICALLY TRANSFORMED PINEAPPLE PLANTS AND METHODS FOR THEIR PRODUCTION," which issued Sep. 14, 1999 to Firoozabady et al. and in the references cited therein and Firoozabady et al. (2002) Molecular Breeding submitted. Additional details relating to organogenic cell culture are described in, e.g., Published International Application No. WO 01/33943, entitled "A METHOD OF PLANT TRANSFORMATION," by Graham et al., which published May 17, 2001, U.S. Pat. No. 5,908,771, entitled "METHOD FOR REGENERATION OF SALVIA SPECIES," which issued Jun. 1, 1999 to Liu et al., U.S. Pat. No. 6,242,257, entitled "TISSUE CULTURE PROCESS FOR PRODUCING A LARGE NUMBER OF VIABLE COTTON PLANTS IN VITRO," which issued Jun. 5, 2001 to Tuli et al., Croy (Ed.) *Plant Molecular Biology Labfax*, Bios Scientific Publishers Ltd. (1993), Jones (Ed.) *Plant Transfer and Expression Protocols*, Humana Press (1995), and in the references cited therein.

One skilled in the art will recognize that many different types of embryogenic and organogenic cells can be used as target cells for the delivery of nucleic acid segments described herein and selection of transformation events. For example, the nucleic acid segments of the invention can be delivered to the cells of the leaf, leaf base, or stem sections as they undergo embryogenesis or organogenesis. Further, nucleic acid segments are optionally delivered to cells immediately after they have given rise to embryogenic -callus or tissue or organogenic callus or tissue. As an additional option, nucleic acid segments can be delivered to embryogenic or organogenic cells after the embryogenic or organogenic material has been maintained and proliferated in vitro for a selected period of time.

X. Nucleic Acid Segment DNA Delivery

The transgenic pineapple cells of the present invention are transformed at various developmental stages, e.g., at various stages of organogenesis or embryogenesis. Further, the nucleic acid segments of the invention can be introduced into pineapple cells in a number of art-recognized ways. In overview, suitable methods of transforming plant cells include microinjection (Crossway et al. (1986) *BioTechniques* 4:320-334), electroporation (Riggs et al. (1986) *Proc. Natl. Acad. Sci. USA* 83:5602-5606, *Agrobacterium*-mediated transformation (Hinchee et al. (1988) *Biotechnology* 6:915-921), ballistic particle acceleration or microprojectile bombardment (Sanford et al. U.S. Pat. No. 4,945,050; and McCabe et al. (1988) *Biotechnology* 6:923-926), pollen-mediated delivery (Zhou et al. (1983) *Methods Enzymol*. 101:433, De Wet et al. (1985) in *The Experimental Manipulation of Ovule Tissues*, Chapman et al. (Eds.), Longman, p. 197; Hess (1987) *Intern. Rev. Cytol.* 107:367; and Luo et al. (1989) *Plant Mol. Biol. Rep.* 7:69), direct nucleic acid transfer to protoplasts of pineapple cells (Caboche et al. (1984) *Comptes Rendus Acad. Sci.* 299, series 3:663), microinjection (Crossway et al. (1986) *Mol. Gen. Genet.* 202:179 and Reich et al. (1986) *Bio/technol.* 4:1001), macroinjection of inflorescence (De la Pena et al. (1987) *Nature* 325:274), whisker-mediated impregnation (Dunahay (1993) *Biotechniques* 15:452-460, and Frame et al. (1994) *The Plant Journal* 6:941-948), laser perforation (Weber (1988) *Naturwissenschaften* 75:35), and ultrasonification (Zhang et al. (1991) Bio/technol. 9:994).

To further illustrate, *Agrobacterium*-mediated transfer is a widely applicable system for introducing genes into plant cells because the nucleic acid segments can be introduced into whole plant tissues, thereby bypassing the need for regeneration of an intact plant from a protoplast. The use of *Agrobacterium*-mediated expression vectors to introduce DNA into plant cells is well known in the art. See, e.g., the methods described by Fraley et al. (1985) *Biotechnology*, 3:629 and Rogers et al. (1987) *Methods in Enzymology* 153:253-277. Further, the integration of T-DNA is a relatively precise process resulting in few rearrangements. The region of DNA to be transferred is defined by the border sequences, and intervening DNA or nucleic acid segment is usually inserted into the plant genome as described by Spielmann et al. (1986) *Mol. Gen. Genet.*, 205:34 and Jorgensen et al. (1987) Mol. Gen. Genet. 207:471.

Modem *Agrobacterium* transformation vectors such as those discussed above are capable of replication in *E. coli* as well as *Agrobacterium*, allowing for convenient manipulations as described by Klee et al., in *Plant DNA Infectious Agents*, Hohn and Schell, (Eds.), Springer-Verlag (1985) pp. 179-203.

Moreover, recent technological advances in vectors for *Agrobacterium*-mediated gene transfer have improved the arrangement of genes and restriction sites in the vectors to facilitate construction of vectors capable of expressing various polypeptide coding genes. For example, the vectors described by Rogers et al. (1987) *Methods in Enzymology*, 153:253, have convenient multi-linker regions flanked by a promoter and a polyadenylation site for direct expression of inserted polypeptide coding genes and are suitable for present purposes. Suitable vectors are described in greater detail above.

In certain embodiment of the invention, heterologous nucleic acid segments are introduced using *Agrobacterium* strains carrying the exogenous DNA in a T-DNA element. The recombinant T-DNA element can either be part of a Ti-plasmid that contains the virulence functions necessary for DNA delivery from *Agrobacterium* cells to plant cells, or the T-DNA element can be present on a plasmid distinct from another plasmid carrying the virulence functions (referred to as binary vectors). A variety of these binary vectors, capable of replication in both *E. coli* and *Agrobacterium*, are described in the references cited above. In one method of co-cultivation, *Agrobacterium* is grown to a concentration of $2-7\times10^8$ cells/ml and is diluted to $1-6\times10^8$ cells/ml, preferably $2-5\times10^8$ cells/ml before co-cultivation. *Agrobacterium* is typically co-cultivated for 1-5 days, preferably for 2-3 days with pineapple tissues.

Suitable *Agrobacterium* strains include *Agrobacterium tumefaciens* and *Agrobacterium rhizogenes*. While wild-type strains may be used, "disarmed" derivatives of both species, in which the tumor-inducing sequences of the Ti plasmid have been removed, are preferred. Suitable *Agrobacterium tumefaciens* strains include, e.g., EHA101, as described by Hood et al. ((1986) *J. Bacteriol.*, 168:1291-1301), LBA4404, as described by Hoekema et al. ((1983) *Nature*, 303:179-80), and C58(pMP90), as described by Koncz and Schell ((1986) *Mol. Gen. Genet.*, 204:383-96). A preferred *Agrobacterium rhizogenes* strain is 15834, as described by Birot et al. (*Biochem*, 25: 323-35).

The pineapple embryogenic or organogenic tissues or callus and the *Agrobacterium* cells carrying the DNA segment are co-cultivated in a suitable co-cultivation medium to allow transfer of the T-DNA to plant cells. After the *Agrobacterium* strain carrying the nucleic acid segment has been prepared, it is usually cultured prior to incubation with the callus or tissue. *Agrobacterium* can be cultured on solid or liquid media according to methods well known to those of skill in the art. See, e.g., U.S. Pat. No. 5,262,316.

As additional options, transformation of plant protoplasts can be achieved using methods based on calcium phosphate precipitation, polyethylene glycol treatment, electroporation, and combinations of these treatments. See, e.g., Potrykus et al. (1985) *Mol. Gen. Genet.*, 199:183; Lorz et al. (1985) *Mol. Gen. Genet.*, 199:178; Fromm et al. (1986) *Nature*, 319:791; Uchimiya et al. (1986) *Mol. Gen. Genet.*, 204:204; Callis et al. (1987) *Genes and Development*, 1:1183; Marcotte et al. (1988) *Nature*, 335:454; Wang et al. (1992) *Bio/Technology*, 10:691-696; and Fennell et al. (1992) *Plant Cell Reports*. 11:567-570.

To transform plant species that cannot be successfully regenerated from protoplasts, other ways to introduce nucleic acid segments into intact cells or tissues can be utilized. For example, "particle gun" or high-velocity microprojectile technology can be utilized. Using such technology, nucleic acid segments are carried through the cell wall and into the cytoplasm on the surface of small metal particles as described in Klein et al. (1987) *Nature*, 327:70; Klein et al. (1988) *Proc. Natl. Acad. Sci. U.S.A.*, 85:8502; and McCabe et al. (1988) *Biotechnology*, 6:923; and Vasil et al. (1992) *Bio/Technology*, 9:667-674. The metal particles penetrate through several layers of cells and thus allow for the transformation of cells within tissue explants. Transformation of tissue explants eliminates the need for passage through a protoplast stage and thus speeds the production of transgenic plants.

Nucleic acid segments can also be introduced into plants by direct DNA transfer into pollen as described by Zhou et al. (1983) *Methods in Enzymology*, 101:433; Hess (1987) *Intern Rev. Cytol.*, 107:367; Luo et al. (1988) *Plant Mol. Biol. Reporter*, 6:165. Expression of polypeptide coding genes can be obtained by injection of the nucleic acid segment into reproductive organs of a plant as described by Pena et al. (1987) *Nature*, 325.:274. Nucleic acid segments can also be injected directly into the cells of immature embryos and the rehydration of desiccated embryos as described by Neuhaus et al. (1987) *Theor. Apl. Genet.*, 75:30; and Benbrook et al., in Proceedings Bio Expo 1986, Butterworth, Stoneham, Mass., pp. 27-54 (1986).

Alternatively, a plant plastid can be transformed directly. Stable transformation of chloroplasts has been reported in higher plants, see, e.g., Svab et al. (1990) *Proc. Nat'l. Acad. Sci. USA* 87:8526-8530; Svab et al. (1993) *Proc. Nat'l Acad. Sci. USA* 90:913-917; Staub et al. (1993) *Embo J.* 12:601-606. The method utilizes particle gun delivery of nucleic acid segments containing a selectable marker and targeting of the nucleic acid to the plastid genome through homologous recombination. In such methods, plastid gene expression can be accomplished by use of a plastid gene promoter or by trans-activation of a silent plastid-borne transgene positioned for expression from a selective promoter sequence such as that recognized by T7 RNA polymerase. The silent plastid gene is activated by expression of the specific RNA polymerase from a nuclear expression construct and targeting of the polymerase to the plastid by use of a transit peptide. Tissue-specific expression may be obtained in such a method by use of a nuclear-encoded and plastid-directed specific RNA polymerase expressed from a suitable plant tissue specific promoter. Such a system has been reported in McBride et al. (1994) *Proc. Natl. Acad. Sci.*, USA 91:7301-7305.

XI. Regeneration and Micropropagation of Transgenic Pineapple Plants

After delivery of nucleic acid segments, the embryogenic or organogenic cells are typically transferred to media that may include a selective agent (e.g., an herbicide or the like) that is capable of preventing the growth of pineapple cells that have not received a gene (e.g., a selectable marker) whose expression product is capable of preventing the action of the selective agent. Selectable markers are described further above. After a period of culture, embryogenic or organogenic callus or tissue that continues to grow normally is separated from embryogenic or organogenic callus or tissue whose growth has been slowed or terminated.

The regeneration of plants from either single plant protoplasts or various explants is well known in the art. See, e.g., Weissbach et al. (Eds.), *Methods for Plant Molecular Biology*, Academic Press, Inc. (1988). In certain embodiments, the regeneration and growth process includes the steps of selection of transformed cells and shoots, rooting the transformed shoots and growth of the plantlets in soil. To illustrate, the regeneration of plants containing a gene introduced by *Agrobacterium* from leaf explants can be achieved as described by Horsch et al. (1985) *Science*, 227:1229-1231. In this procedure, transformants are grown in the presence of a selection agent and in a medium that induces the regeneration of shoots in the plant species being transformed as described by Fraley et al. (1983) *Proc. Natl. Acad. Sci. U.S.A.*, 80:4803. This procedure typically produces shoots within two to four weeks and these transformed shoots are then transferred to an appropriate root-inducing medium containing the selective agent and an antibiotic to prevent bacterial growth. For pineapple, leaf bases may be used to produce organogenic materials (Firoozabady and Moy (2003) "Regeneration of pineapple plants via somatic embryogenesis and organogenesis," In Vitro in press), and then these materials may be exposed to *Agrobacterium* to produce, upon selection perhaps, transgenic organogenic materials. These materials then are induced to produce shoots and complete plants. In certain embodiments, transformation of embryogenic callus is preferred for forming transformed plant shoots. Transformed shoots that rooted in the presence of the selective agent to form plantlets are then transplanted to soil or other media to allow the production of roots.

Additional details relating to plant regeneration, micropropagation, and other aspects that are adapted for use in the methods of the present invention are provided in, e.g., U.S. Pat. No. 5,952,543 and WO 01/33943 (referenced above), U.S. Pat. Nos. 5,591,616, 6,037,522, European Pat. Application Nos. 604662 (A1) and 672752 (A1), and WO 01/12828. See also, Kyte et al., *Plants from Test Tubes: An Introduction to Micropropagation*, Timber Press, Inc. (1996), Hudson et al., *Hartmann and Kester's Plant Propagation: Principles and Practices* 7$^{th}$ Ed., Pearson Education (2001), Bajaj (Ed.) *High-Tech and Micropropagation I*, Springer-Verlag New York, Inc. (1992), Jain, *In Vitro Haploid Production in Higher Plants*, Kluwer Academic Publishers (1996), and Debergh et al. (Eds.), *Micropropagation: Technology and Application*, Kluwer Academic Publishers (1991).

Optionally, carotenoid biosynthetic polypeptides of the invention can be recovered and purified from transformed pineapple cell cultures or transformed pineapple plant tissues (e.g., fruit tissues or the like) by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. In some cases the protein will need to be refolded to recover a functional product. In addition to the references noted supra, a variety of purification methods are well known in the art, including, e.g., those set forth in Sandana, *Bioseparation of Proteins*, Academic Press, Inc. (1997); and Bollag et al., *Protein Methods*, 2nd Ed., Wiley-Liss, NY (1996); Walker, *The Protein Protocols Handbook*, Humana Press, NJ (1996); Harris and Angal, *Protein Purification Applications: A Practical Approach*, IRL Press (1990); Scopes, *Protein Purification: Principles and Practice*, 3rd Ed., Springer Verlag (1993); and Janson et al., *Protein Purification: Principles, High Resolution Methods and Applications*, 2$^{nd}$ Ed., Wiley-VCH (1998).

XII. EXAMPLES

The following examples are offered to illustrate, but not to limit the claimed invention.

Media are designated with letters and numbers; letters refer to media components used, followed by a number that indicates the concentration of the particular component. For example, B2N2 is an MS media that contains 6-benzylamino purine (13A or B) and α-naphthalene acetic acid (NAA or N). More specific details relating to the media compositions referred to in these examples, including component concentrations, are provided below.

Example 1

Introduction of Phyotene Synthase Gene (PSY) Gene from Tangerine into Pineapple (Transgenic Line 16.5.9)

1. Isolation of PSY Gene from Citrus
   i. Primer Design
   Two primers were designed based on the sequence information of PSY-Naval (Accession No. Gi 5959859):

```
Forward primer PSY-F:
5'-aaa ctg cag atg tct gtt aca ttg ctg tgg-3'

Reverse primer PSY-R:
5'-gat atc tta agc ctt act ggt ata tat tct tg-3'
``` ii. RNA Isolation
   Total RNA was extracted from Tangerine leaf tissue with Trizol solution (Invitrogen, Inc., CA, USA). The extraction was performed according to the manufacture's procedure.
   iii. Reverse Transcription Reaction
   Reverse transcription was carried out with 1 μg of total RNA and 1 μl of 10 μM PSY-R primer in 20 μl reaction volume.
   iv. PCR to Isolate PSY Gene
   PCR was performed with PSY-F and PSY-R primers in following reaction:
   PSY-F (10 μM): 1 μl
   PSY-R (10 μM): 1 μl
   Reverse reaction: 1 μl
   DNTPs (10 mM): 1 μl
   10× buffer: 2.5 μl
   Pfu DNA polymerase: 0.2 μl
   Water to 25 μl
   The PCR program was: 92° C. for 2 minutes to denature. Then 35 cycles of:
   92° C. for 30 seconds
   55° C. for 20 seconds
   72° C. for 1.5 min.
   v. Cloning the PCR Fragment.
   The PCR reaction product or fragment was run on 0.8% Agrose gel. The PCR fragment was cut off and purified using Qiagen's Gel purification Kit (Qiagen, Inc., CA, USA). The fragment was then cloned into pGEM-Teasy vector (Promega Corp., WI, USA). Sequencing was done using T7 and M13-R primers.

2. Establishment of Shoot Cultures
   Meristems isolated from crowns of Del Monte Gold MD-2 pineapples grown in the field in Costa Rica were used to establish shoot cultures. Briefly, leaves of the crowns were removed by hand and discarded, the core or the stem of the crown (~3×5 cm) was washed in water, surface sterilized with 33% Clorox plus 0.05% Tween20 with stiring for 25 minutes and rinsed twice in sterile water. The lateral meristems and crown tip meristem were excised from the core by removing primary leaves one by one, while flaming the tools frequently. The crown tip meristem explant including the meristem dome, 2-3 tiny primary leaves, and 1 cm³ of the stem core was placed on the shoot culture medium B2N2±CC. The lateral meristems were also isolated along with 1 cm³ of the stem core and cultured on the same medium. CC (500 mg/l each of carb and cefotaxime) were used to kill off endogenous microbial contamination. Cultures were incubated under continuous light at 28° C. Nine days after culture initiation, the tissues were subcultured onto B2N2+N. Nystatin (N, 40 mg/l) was used to kill off endogenous yeast and fungal contaminations. After 20 days, crown tip leaves had grown long, these were removed to promote the growth of crown tip meristem and were transferred to fresh B2N2+NA medium. Amphicilin B (A, 5 mg/l) was used also kill off any residual endogenous yeast and fungal contaminations. After two additional weeks, buds were formed (2-3 per explant) and subsequently new small shoots were produced to form a cluster of shoots. After a total of 4 months from culture initiation, shoot clusters were transferred and maintained in liquid B1.5N.5 medium with monthly subculture.

3. Prereatment of Explants for Cocultivation with *Agrobacterium*
   Rapidly growing shoots were used as explants. Tips of the long leaves (>15 mm) were cut off to provide smaller explants. Shoots were cut longitudinally into 4-6 sections and pretreated (cultured) on P10T1.1B6 (containing 6% banana pulp) for 8 days. Leaf bases and core sections were prepared and were mixed with *Agrobacterium* for cocultivation.

4. *Agrobacterium Tumefaciens* Culture and Preparation
   *Agrobacterium tumefaciens* strain GV3101 containing a binary vector system was used for transformation. The vector system included vector pDM comprising a surB gene for conferring chlorsulfuron resistance, and the psy gene for expressing the phytoene synthase gene. Bacteria were taken out of frozen glycerol, cultured, and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacteria concentration was determined, using a spectrophotometer (Beckman DU-50) before cocultivation, and was shown to be 4×10⁸ cells/ml.

5. Cocultivation of Cocultivation Medium
   Bacteria were mixed at the volume ratio of 4:1 (plant tissue: *Agrobacterium* cells) with 170 leaf bases and core sections, tissue was blotted dry and the mixture was placed on 7.0 cm sterile Fisherbrand G6 glass filter circles on the top of cocultivation medium P10T2.2As300. Plates were parafilmed and placed in a 24° C. controlled environment incubator in the dark for 3 days.

6. Recovery, Selection, and Plant Regeneration
   After cocultivation, tissues were transferred (15-20 pieces/plate) to recovery medium P10T1.1Carb500 for a recovery period of 7 days under low light condition (16 hrs/day). The explants then were transferred to selection medium P10T2.2Carb300CS5 for 17 days then to P10T2.2Carb500CS5 as bacterial growth was seen and incubated under high light intensity (16 hrs/day). Carbenicillin was used to kill off the residual *Agrobacterium* and chlorsulfuron (CS) to select for transformed cells. On selection medium, most of the tissues turned brown within 3-6 weeks, however, occasionally some sectors of the tissues remained healthy and started growing to produce green healthy morphogenic tissue. Morphogenic tissues produced transgenic shoot on B3N.2Carb100CS10 medium within 30 days. These were then transferred to B1Carb100CS10 to elongate. Some of the shoots were vitrified, which then were transferred to B1A1% Carb100CS10 for 14 days to produce elongated normal shoots.

7. Confirmation of Transformation

Shoots were confirmed to be transformed by various means: 1. CS resistant shoots or shoot primordia remained healthy and green on lethal levels of CS, 2. CS resistant shoots or shoot primordia were sampled (2-5 mg/resistant piece) for a GUS assay. Transformed tissues stained blue and nontransformed tissues did not stain blue. Tissues can also be tested molecularly for transfomation using, e.g., PCR and Southern blotting analysis.

8. Micropropagation and Production of Transgenic Plants

Individual or small shoot clusters were transferred to 15 ml liquid medium B1Carb100CS20 in GA-7 cubes (2-3 clusters/cube) for propagation and growth. Optionally, 30 days later, shoot clusters can be micropropagated and maintained in B1.5N.5CS20 (containing no counterselective agents) for several months. The individual shoots (4-6 cm long) were separated and cultured in liquid rooting medium N.5IBA.5CS10 or N.5IBA.5CS20 (containing no counterselective agents) for 24 weeks to produce complete plants. Plants can then be transplanted in soil, hardened off gradually, and transferred to the greenhouse conditions.

Example 2

Introduction of Phyotene Synthase Gene (PSY) Gene from Tangerine into Pineapple (13.18.2)

1. Isolation of Psy Gene from *Citrus*

Same as example 1.

2. Preparation of Source Tissues i. Establishment of Shoot Cultures.

Same as example 1.

ii. Pretreatment of Explants for Cocultivation with *Agrobacterium*.

Rapidly growing shoots cultured as above for 4 months were used as explants. Tips of the long leaves (>15 mm) were cut off to provide smaller explants. Shoots were cut longitudinally into 3-8 sections and pretreated (cultured) on P2T10A medium for 10 days. Leaf bases and core sections were prepared and pretreated again on the same media for 62 days prior to transfer to another pretreatment medium. The sections with morphogenic tissues containing shoot primordial were subcultured onto T1.1I.1medium for 24 days. Organogenic tissues then were subcultured on B3N.2 medium for 22 days, then were cut into 3-5 mm sections and placed on B2N2 medium for 7 days, and then mixed with *Agrobacterium* for cocultivation.

3. *Agrobacterium Tumefaciens* Culture and Preparation

*Agrobacterium tumefaciens* strain GV3101 containing the binary vectors, which is referred to above, was used for transformation. As mentioned, vector pDM contains the surB gene, which confers chlorsulfuron resistance and the psy gene expresses the phyotene synthase gene. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacteria concentration was determined, using a spectrophotometer (Beckman DU-50) before cocultivation, and was shown to be $1.7 \times 10^9$ cells/ml.

4. Cocultivation of Cocultivation Medium

Bacteria were mixed at the volume ratio of 4:1 (plant tissue:*Agrobacterium* cells), tissue was blotted dry, and the mixture was placed on 7.0 cm sterile Fisherbrand G6 glass filter circles on the top of cocultivation medium B3N.2AS300. Plates were parafilmed and placed in a 24° C. controlled environment incubator in the dark for 3 days.

5. Recovery, Selection and Regeneration

After cocultivation, tissues were transferred (20-25 pieces/plate) to recovery medium B3N.2Carb500 and B3N.2CEF400 for a recovery period of 7 days under low light condition (16 hrs/day). The explants were then transferred to selection medium B2N2CEF400CS5 under high light intensity (16 hrs/day) for 25 days and then on B3N.2CEF400CS5 with monthly subculturing thereafter. Cefotaxime was used to kill off the residual *Agrobacterium* and chlorsulfuron (CS) to select for transformed cells. On selection medium, most of the tissues turned brown within 4-6 weeks, however, two sectors of the tissues remained healthy and started growing to produce green healthy morphogenic tissue. Plants were regenerated as described in Example 1.

6. Confirmation of Transformation

Same as Example 1.

7. Micropropagation and Production of Transgenic Plants

Same as Example 1.

| MEDIA COMPOSITIONS Minimal Asuc = MinAsuc | | |
|---|---|---|
| | preferred | range |
| potassium phosphate dibasic | 10.5 g/l | 5-20 g/l |
| potassium phosphate monobasic | 4.5 g/l | 2-8 g/l |
| ammonium sulfate | 1.0 g/l | 0.5-3 g/l |
| sodium citrate dihydrate | 0.5 g/l | 0-2 g/l |
| magnesium sulfate heptahydrate | 247 mg/l | 0-1000 g/l |
| glucose | 2.0 g/l | 1-30 g/l |

MinAsuc

MinA but with sucrose instead of glucose.

| L-Broth: | |
|---|---|
| Tryptone | 10 g/l |
| Yeast Extract | 5 g/l |
| NaCl | 5 g/l |
| Glucose | 1 g/l |
| pH | 7.0-7.2 |
| Bacto Agar | 15 g/l |

For tissue culture media, the pH should be in the range of about 5-7.5, preferably about 5.6. The medium is used following sterilization by autoclaving, except for specific components that are filter-sterilized and then added after autoclaving.

| MS | |
|---|---|
| MS salts | 1X |
| B5 vitamins | 1X |
| Sucrose | 30 g/l |
| MES | 600 mg/l |
| Gel-rite ® | 2.5 g/l |
| pH | 5.7 |

-continued

| B1.5N.5 | |
|---|---|
| MS medium + | 1.5 mg/l |
| BA | |
| NAA | 0.5 mg/l |
| B2N2 | |
| MS medium + | 2 mg/l |
| BA | |
| NAA | 2 mg/l |
| B2N2 + CC | |
| MS medium + | 2 mg/l |
| BA | |
| NAA | 2 mg/l |
| Carbenicillin | 500 mg/l |
| Cefotaxime | 500 mg/l |
| B2N2CEF400CS5 | |
| MS medium + | 2 mg/l |
| BA | |
| NAA | 2 mg/l |
| Cefotaxime | 400 mg/l |
| Chlorsulfuron | 5 µg/l |
| B2N2 + N | |
| B2N2 + Nystatin | 40 mg/l |
| B2N2 + NA | |
| B2N2 medium + | 40 mg/l |
| Nystatin | |
| Amphotericin B | 5 mg/l |
| B3N.2 | |
| MS + | 3 mg/l |
| BA | |
| NAA | 0.2 mg/l |
| B3N.2AS300 | |
| B3N.2 + Acetosyringone | 300 µM |
| B3N.2CARB500 | |
| B3N.2 + Carbenicillin | 500 mg/l |
| B3N.2CEF400 | |
| B3N.2 + Cefotaxime | 400 mg/l |
| B3N.2CEF400CS5 | |
| B3N.2Cef400 + Chlorsulfuron | 5 µg/l |
| P2T10A | |
| MS with agar instead of Gel-rite + | 2 mg/l |
| Picloram | |
| Thidiazuron | 10 mg/l |
| P10T1.1B6 | |
| MS + | 10 mg/l |
| Picloram | |
| Thidiazuron | 1.1 mg/l |
| Banana Pulp | 6% |
| P10T1.1CARB500 | |
| MS + | 10 mg/l |
| Picloram | |
| Thidiazuron | 1.1 mg/l |
| Carbenicillin | 500 mg/l |
| P10T2.2 | |
| MS + | 10 mg/l |
| Picloram | |
| Thidiazuron | 2.2 mg/l |
| P10T2.2A | |
| P10T2.2 with agar instead of gel-rite | |
| P10T2.2AS300 | |
| MS + | 10 mg/l |
| Picloram | |

-continued

| | |
|---|---|
| Thidiazuron | 2.2 mg/l |
| Acetosyringone | 300 µM |
| P10T2.2CARB300CS5 | |
| MS + | 10 mg/l |
| Picloram | |
| Thidiazuron | 2.2 mg/l |
| Carbenicillin | 300 mg/l |
| Chlorsulfuron | 5 µg/l |
| P10T2.2CARB500CS5 | |
| MS + | 10 mg/l |
| Picloram | |
| Thidiazuron | 2.2 mg/l |
| Carbenicillin | 500 mg/l |
| Chlorsulfuron | 5 µg/l |
| P10B.5 | |
| MS + | 10 mg/l |
| Picloram | |
| BA | 0.5 mg/l |
| N.5I.5 LIQUID | |
| MS without Gel-rite + | 0.5 mg/l |
| NAA | |
| IBA | 0.5 mg/l |
| T1.1I.1 | |
| MS + | 1.1 mg/l |
| Thidiazuron | |
| IBA | 0.1 mg/l |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of controlling carotenoid accumulation in at least one pineapple cell, the method comprising introducing at least one carotenoid biosynthetic polypeptide expression regulator into said pineapple cell, wherein said carotenoid biosynthetic polypeptide expression regulator controls accumulation of carotenoid in said pineapple cell, and wherein said carotenoid biosynthetic polypeptide expression regulator comprises at least one nucleic acid segment in a sense or antisense orientation to a coding nucleic acid that encodes at least one carotenoid biosynthetic polypeptide, which nucleic acid segment stably integrates into the genome of said pineapple cell.

2. The method of claim 1, wherein said pineapple cell is an embryogenic cell, an embryogenic callus cell, an organogenic cell, or an organogenic callus cell.

3. The method of claim 1, wherein said carotenoid biosynthetic polypeptide expression regulator controls accumulation of one or more carotenoids that are selected from group consisting of: phytoene, phytofluene, ζ-carotene, neurosporene, δ-carotene, γ-carotene, α-carotene, β-carotene, apocarotenal, lycopene, canthaxanthin, zeathanthin, and lutein.

4. The method of claim 1, wherein said nucleic acid segment is linked to a selectable marker.

5. The method of claim 1, wherein said nucleic acid segment is operably linked to a constitutive promoter, a tissue-specific promoter or to an inducible promoter.

6. The method of claim 1, wherein said pineapple cell is an organogenic cell produced by culturing at least one meristemic cell.

7. The method of claim 6, wherein said meristemic cell is a non-apical meristemic cell.

8. The method of claim 6, wherein said culturing comprises culturing said meristemic cell to produce at least one shoot, and culturing at least one explant from said shoot to produce said organogenic cell.

9. A method of altering pineapple fruit coloration, the method comprising introducing at least one carotenoid biosynthetic polypeptide expression regulator into at least one pineapple plant, wherein said carotenoid biosynthetic polypeptide expression regulator controls accumulation of at least one colored carotenoid in said pineapple fruit, thereby altering said coloration of said pineapple fruit, and wherein said carotenoid biosynthetic polypeptide expression regulator comprises at least one nucleic acid segment in a sense or antisense orientation to a coding nucleic acid that encodes at least one carotenoid biosynthetic polypeptide, which nucleic acid segment stably integrates into the genome of said pineapple plant.

10. The method of claim 9, wherein said colored carotenoid is selected from group consisting of: phytoene, phytofluene, ζ-carotene, neurosporene, δ-carotene, γ-carotene, α-carotene, β-carotene, apocarotenal, lycopene, canthaxanthin, zeathanthin, and lutein.

11. The method of claim 9, wherein said carotenoid biosynthetic polypeptide expression regulator is introduced into at least one pineapple cell from which said pineapple plant is regenerated.

12. A pineapple cell that comprises at least one introduced carotenoid biosynthetic polypeptide expression regulator, which carotenoid biosynthetic polypeptide expression regulator controls accumulation of carotenoid in said pineapple cell, and wherein said carotenoid biosynthetic polypeptide expression regulator comprises at least one nucleic acid segment in a sense or antisense orientation to a coding nucleic acid that encodes at least one carotenoid biosynthetic polypeptide that is selected from the group consisting of: an isopentenyl diphosphate isomerase, a geranylgeranyl pyrophosphate synthase, a phytoene synthase, a phytoene desaturase, a ζ-carotene desaturase, a lycopene β-cyclase, a lycopene ε-cyclase, a β-carotene hydroxylase, and an ε-hydroxylase.

13. The pineapple cell of claim 12, wherein said pineapple cell is an embryogenic cell, an embryogenic callus cell, an organogenic cell, or an organogenic callus cell.

14. The method of claim 12, wherein said carotenoid biosynthetic polypeptide expression regulator controls accumulation of one or more carotenoids that are selected from group consisting of: phytoene, phytofluene, ζ-carotene, neurosporene, δ-carotene, γ-carotene, α-carotene, β-carotene, apocarotenal, lycopene, canthaxanthin, zeathanthin, and lutein.

15. A pineapple plant that that is generated from said pineapple cell of claim 12.

16. The method of claim 1, wherein said carotenoid biosynthetic polypeptide expression regulator comprises at least one nucleic acid segment selected from:
(a) a sense nucleic acid segment that corresponds to at least a portion of at least one endogenous carotenoid biosynthetic polypeptide gene; and
(b) an antisense nucleic acid segment that corresponds to at least a portion of at least one endogenous carotenoid biosynthetic polypeptide gene.

17. The method of claim 1, wherein said carotenoid biosynthetic polypeptide expression regulator comprises at least one nucleic acid segment, which when expressed in said pineapple cell, produces a double stranded RNA (dsRNA) that targets the destruction of a target endogenous mRNA encoding a carotenoid biosynthetic polypeptide.

18. The method of claim 1, wherein said pineapple cell further comprises at least a second carotenoid biosynthetic polypeptide expression regulator comprising at least one nucleic acid segment, which when expressed in said pineapple cell, produces a double stranded RNA (dsRNA) that targets the destruction of a target endogenous mRNA encoding a carotenoid biosynthetic polypeptide.

19. The method of claim 9, wherein said carotenoid biosynthetic polypeptide expression regulator comprises at least one nucleic acid segment selected from:
(a) a sense nucleic acid segment that corresponds to at least a portion of at least one endogenous carotenoid biosynthetic polypeptide gene; and
(b) an antisense nucleic acid segment that corresponds to at least a portion of at least one endogenous carotenoid biosynthetic polypeptide gene.

20. The method of claim 9, wherein said carotenoid biosynthetic polypeptide expression regulator comprises at least one nucleic acid segment, which when expressed in said pineapple cell, produces a double stranded RNA (dsRNA) that targets the destruction of a target endogenous mRNA encoding a carotenoid biosynthetic polypeptide.

21. The method of claim 9, wherein said pineapple plant further comprises at least a second carotenoid biosynthetic polypeptide expression regulator comprising at least one nucleic acid segment, which when expressed in said pineapple plant, produces a double stranded RNA (dsRNA) that targets the destruction of a target endogenous mRNA encoding a carotenoid biosynthetic polypeptide.

22. The pineapple cell of claim 12, wherein said carotenoid biosynthetic polypeptide expression regulator comprises at least one nucleic acid segment selected from:
(a) a sense nucleic acid segment that corresponds to at least a portion of at least one endogenous carotenoid biosynthetic polypeptide gene;
(b) an antisense nucleic acid segment that corresponds to at least a portion of at least one endogenous carotenoid biosynthetic polypeptide gene.

23. The pineapple cell of claim 12, wherein said carotenoid biosynthetic polypeptide expression regulator comprises at least one nucleic acid segment, which when expressed in said pineapple cell produces a double stranded RNA (dsRNA) that targets the destruction of a target endogenous mRNA encoding a carotenoid biosynthetic polypeptide.

24. The pineapple cell of claim 12, wherein said pineapple cell further comprises at least a second carotenoid biosynthetic polypeptide expression regulator comprising at least one nucleic acid segment, which when expressed in said pineapple plant produces a double stranded RNA (dsRNA) that targets the destruction of a target endogenous mRNA encoding a carotenoid biosynthetic polypeptide.

25. A method of modifying the level of lycopene in a pineapple plant, the method comprising expressing a carotenoid biosynthetic polypeptide expression regulator comprising an RNA that suppresses endogenous lycopene β-cyclase or endogenous lycopene ε-cyclase expression.

26. The method of claim 25, wherein the carotenoid biosynthetic polypeptide expression regulator is a sense nucleic acid segment corresponding to a coding region of the lycopene β-cyclase or the lycopene ε-cyclase.

* * * * *

UNITED STATES PATENT AND TRADEMARK OFFICE
CERTIFICATE OF CORRECTION

| | | |
|---|---|---|
| PATENT NO. | : 7,663,021 B2 | Page 1 of 1 |
| APPLICATION NO. | : 10/536888 | |
| DATED | : February 16, 2010 | |
| INVENTOR(S) | : Thomas R. Young et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Column 41,

Claim 14, line 1 delete "method" and insert --pineapple cell--

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,663,021 B2 | Page 1 of 1 |
| APPLICATION NO. | : 10/536888 | |
| DATED | : February 16, 2010 | |
| INVENTOR(S) | : Thomas R. Young et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Column 41, line 50, (Claim 14, line 1) delete "method" and insert --pineapple cell--

This certificate supersedes the Certificate of Correction issued November 2, 2010.

Signed and Sealed this

Seventh Day of December, 2010

David J. Kappos
*Director of the United States Patent and Trademark Office*